(12) United States Patent
Satish et al.

(10) Patent No.: US 9,936,906 B2
(45) Date of Patent: Apr. 10, 2018

(54) SYSTEM AND METHODS FOR MANAGING BLOOD LOSS OF A PATIENT

(71) Applicant: Gauss Surgical, Inc., Los Altos, CA (US)

(72) Inventors: Siddarth Satish, Cupertino, CA (US); Ali Zandifar, San Francisco, CA (US); Kevin J Miller, Mountain View, CA (US)

(73) Assignee: Gauss Surgical, Inc., Los Altos, CA (US)

( * ) Notice: Subject to any disclaimer, the term of this patent is extended or adjusted under 35 U.S.C. 154(b) by 410 days.

(21) Appl. No.: 13/894,054

(22) Filed: May 14, 2013

(65) Prior Publication Data

US 2013/0303870 A1 Nov. 14, 2013

Related U.S. Application Data

(60) Provisional application No. 61/776,577, filed on Mar. 11, 2013, provisional application No. 61/646,822, (Continued)

(51) Int. Cl.
*A61B 5/00* (2006.01)
*A61B 5/145* (2006.01)
(Continued)

(52) U.S. Cl.
CPC ........ *A61B 5/14535* (2013.01); *A61B 5/0082* (2013.01); *A61B 5/02028* (2013.01);
(Continued)

(58) Field of Classification Search
CPC .............. A61B 5/14535; A61B 5/4875; A61B 5/02042; A61B 5/4848; A61B 5/7278;
(Continued)

(56) References Cited

U.S. PATENT DOCUMENTS 2,707,955 A 5/1955 Borden
3,182,252 A 5/1965 van den Berg
(Continued)

FOREIGN PATENT DOCUMENTS

CA 2870635 A1 10/2013
CN 101505813 8/2009
(Continued)

OTHER PUBLICATIONS

Sant, et al. "Exsanguinated Blood Volume Estimation Using Fractal Analysis of Digital Images." Journal of Forensic Sciences 57.3 (2012): 610-17. Print.
(Continued)

*Primary Examiner* — Tiffany Weston
(74) *Attorney, Agent, or Firm* — Cooley LLP

(57) ABSTRACT

One variation of the method for managing blood loss of a patient includes: receiving an image of a physical sample; extracting a feature from an area of the image corresponding to the physical sample; estimating a blood volume indicator of the physical sample according to the extracted feature; estimating a patient blood loss based on the blood volume indicator; estimating a euvolemic patient hematocrit based on an estimated patient blood volume and the estimated patient blood loss; receiving a measured patient hematocrit; and generating a volemic status indicator based on a comparison between the measured patient hematocrit and the estimated euvolemic patient hematocrit.

19 Claims, 14 Drawing Sheets

Related U.S. Application Data filed on May 14, 2012, provisional application No. 61/722,780, filed on Nov. 5, 2012.

(51) Int. Cl.
*A61B 5/02* (2006.01)
*G01N 33/49* (2006.01)
*G01N 15/14* (2006.01)

(52) U.S. Cl.
CPC ........ *A61B 5/02042* (2013.01); *A61B 5/4848* (2013.01); *A61B 5/4875* (2013.01); *A61B 5/7278* (2013.01); *G01N 33/49* (2013.01); *A61B 5/742* (2013.01); *A61B 2576/00* (2013.01); *G01N 2015/1472* (2013.01)

(58) Field of Classification Search
CPC ... A61B 5/02028; A61B 5/0082; A61B 5/742; A61B 2576/00; G01N 33/49; G01N 2015/1472
USPC .... 600/366, 368, 369, 371; 1/366, 368, 369, 1/371
See application file for complete search history.

(56) References Cited

U.S. PATENT DOCUMENTS

| | | |
|---|---|---|
| 3,199,507 A | 8/1965 | Kamm |
| 3,367,431 A | 2/1968 | Prindle Baker |
| 3,646,938 A | 3/1972 | Haswell |
| 3,832,135 A | 8/1974 | Chlupsa et al. |
| 3,864,571 A | 2/1975 | Stillman et al. |
| 3,948,390 A | 4/1976 | Ferreri |
| 4,105,019 A | 8/1978 | Haswell |
| 4,149,537 A | 4/1979 | Haswell |
| 4,244,369 A | 1/1981 | McAvinn et al. |
| 4,402,373 A | 9/1983 | Comeau |
| 4,422,548 A | 12/1983 | Cheesman et al. |
| 4,429,789 A | 2/1984 | Puckett |
| 4,562,842 A | 1/1986 | Morfeld et al. |
| 4,583,546 A | 4/1986 | Garde |
| 4,773,423 A * | 9/1988 | Hakky ................ A61M 1/3678 600/309 |
| 4,784,267 A | 11/1988 | Gessler et al. |
| 4,832,198 A | 5/1989 | Alikhan |
| 4,917,694 A | 4/1990 | Jessup |
| 4,922,922 A | 5/1990 | Pollock et al. |
| 5,029,584 A | 7/1991 | Smith |
| 5,031,642 A | 7/1991 | Nosek |
| 5,048,683 A | 9/1991 | Westlake |
| 5,119,814 A | 6/1992 | Minnich |
| 5,132,087 A | 6/1992 | Manion et al. |
| 5,190,059 A | 3/1993 | Fabian et al. |
| 5,231,032 A | 7/1993 | Ludvigsen |
| 5,236,664 A * | 8/1993 | Ludvigsen ......... A61B 5/02042 204/416 |
| 5,285,682 A | 2/1994 | Micklish |
| 5,492,537 A | 2/1996 | Vancaillie |
| 5,522,805 A | 6/1996 | Vancaillie et al. |
| 5,629,498 A | 5/1997 | Pollock et al. |
| 5,633,166 A | 5/1997 | Westgard et al. |
| 5,650,596 A | 7/1997 | Morris et al. |
| 5,709,670 A | 1/1998 | Vancaillie et al. |
| 5,807,358 A | 9/1998 | Herweck et al. |
| 5,851,835 A | 12/1998 | Groner |
| 5,923,001 A | 7/1999 | Morris et al. |
| 5,931,824 A | 8/1999 | Stewart et al. |
| 5,944,668 A | 8/1999 | Vancaillie et al. |
| 5,956,130 A | 9/1999 | Vancaillie et al. |
| 5,984,893 A | 11/1999 | Ward |
| 5,996,889 A | 12/1999 | Fuchs et al. |
| 6,006,119 A | 12/1999 | Soller et al. |
| 6,061,583 A | 5/2000 | Ishihara et al. |
| 6,359,683 B1 | 3/2002 | Berndt |
| 6,510,330 B1 | 1/2003 | Enejder |
| 6,641,039 B2 | 11/2003 | Southard |
| 6,728,561 B2 | 4/2004 | Smith et al. |
| 6,730,054 B2 | 5/2004 | Pierce et al. |
| 6,777,623 B2 | 8/2004 | Ballard |
| 6,998,541 B2 | 2/2006 | Morris et al. |
| 7,001,366 B2 | 2/2006 | Ballard |
| 7,112,273 B2 | 9/2006 | Weigel et al. |
| 7,147,626 B2 | 12/2006 | Goodman et al. |
| 7,158,030 B2 | 1/2007 | Chung |
| 7,180,014 B2 | 2/2007 | Farber et al. |
| 7,274,947 B2 | 9/2007 | Koo et al. |
| 7,297,834 B1 | 11/2007 | Shapiro |
| 7,299,981 B2 | 11/2007 | Hickle et al. |
| 7,364,545 B2 | 4/2008 | Klein |
| 7,384,399 B2 | 6/2008 | Ghajar |
| 7,430,047 B2 | 9/2008 | Budd et al. |
| 7,430,478 B2 | 9/2008 | Fletcher-Haynes et al. |
| 7,469,727 B2 | 12/2008 | Marshall |
| 7,499,581 B2 | 3/2009 | Tribble et al. |
| 7,557,710 B2 | 7/2009 | Sanchez et al. |
| 7,641,612 B1 | 1/2010 | McCall |
| D611,731 S | 3/2010 | Levine |
| 7,670,289 B1 | 3/2010 | McCall |
| 7,703,674 B2 | 4/2010 | Stewart |
| 7,708,700 B2 | 5/2010 | Ghajar |
| 7,711,403 B2 | 5/2010 | Jay et al. |
| 7,749,217 B2 | 7/2010 | Podhajsky |
| 7,795,491 B2 | 9/2010 | Stewart et al. |
| 7,819,818 B2 | 10/2010 | Ghajar |
| 7,909,806 B2 | 3/2011 | Goodman et al. |
| 7,966,269 B2 | 6/2011 | Bauer et al. |
| 7,995,816 B2 | 8/2011 | Roger et al. |
| 8,025,173 B2 | 9/2011 | Michaels |
| 8,105,296 B2 | 1/2012 | Morris et al. |
| 8,181,860 B2 | 5/2012 | Fleck et al. |
| 8,194,235 B2 | 6/2012 | Kosaka et al. |
| 8,279,068 B2 | 10/2012 | Morris et al. |
| 8,398,546 B2 | 3/2013 | Pacione et al. |
| 8,472,693 B2 | 6/2013 | Davis et al. |
| 8,479,989 B2 | 7/2013 | Fleck et al. |
| 8,576,076 B2 | 11/2013 | Morris et al. |
| 8,626,268 B2 | 1/2014 | Adler et al. |
| 8,693,753 B2 | 4/2014 | Nakamura |
| 8,704,178 B1 | 4/2014 | Pollock et al. |
| 8,792,693 B2 | 7/2014 | Satish et al. |
| 8,897,523 B2 | 11/2014 | Satish et al. |
| 8,983,167 B2 | 3/2015 | Satish et al. |
| 9,171,368 B2 | 10/2015 | Satish et al. |
| 2003/0095197 A1 | 5/2003 | Wheeler et al. |
| 2003/0130596 A1 | 7/2003 | Goltz |
| 2004/0031626 A1 | 2/2004 | Morris et al. |
| 2004/0129678 A1 | 7/2004 | Crowley et al. |
| 2005/0051466 A1 | 3/2005 | Carter et al. |
| 2005/0163354 A1* | 7/2005 | Ziegler ................ G01N 15/05 382/128 |
| 2006/0058593 A1 | 3/2006 | Drinan et al. |
| 2006/0178578 A1 | 8/2006 | Tribble et al. |
| 2006/0224086 A1 | 10/2006 | Harty |
| 2007/0004959 A1 | 1/2007 | Carrier et al. |
| 2007/0287182 A1 | 12/2007 | Morris et al. |
| 2008/0029416 A1 | 2/2008 | Paxton |
| 2008/0030303 A1 | 2/2008 | Kobren et al. |
| 2008/0045845 A1 | 2/2008 | Pfeiffer et al. |
| 2008/0194906 A1 | 8/2008 | Mahony et al. |
| 2009/0076470 A1 | 3/2009 | Ryan |
| 2009/0310123 A1 | 12/2009 | Thomson |
| 2009/0317002 A1 | 12/2009 | Dein |
| 2010/0003714 A1 | 1/2010 | Bachur, Jr. et al. |
| 2010/0007727 A1 | 1/2010 | Torre-Bueno |
| 2010/0025336 A1 | 2/2010 | Carter et al. |
| 2010/0027868 A1 | 2/2010 | Kosaka et al. |
| 2010/0066996 A1 | 3/2010 | Kosaka et al. |
| 2010/0087770 A1 | 4/2010 | Bock et al. |
| 2010/0280117 A1 | 11/2010 | Patrick et al. |
| 2011/0192745 A1 | 8/2011 | Min |
| 2011/0196321 A1 | 8/2011 | Wudyka |
| 2011/0200239 A1 | 8/2011 | Levine et al. |
| 2011/0275957 A1 | 11/2011 | Bhandari |

(56) References Cited

U.S. PATENT DOCUMENTS

| | | | |
|---|---|---|---|
| 2011/0305376 | A1 | 12/2011 | Neff |
| 2011/0316973 | A1 | 12/2011 | Miller et al. |
| 2012/0000297 | A1 | 1/2012 | Hashizume et al. |
| 2012/0065482 | A1 | 3/2012 | Robinson et al. |
| 2012/0210778 | A1 | 8/2012 | Palmer et al. |
| 2012/0257188 | A1 | 10/2012 | Yan et al. |
| 2012/0262704 | A1 | 10/2012 | Zahniser et al. |
| 2012/0309636 | A1 | 12/2012 | Gibbons et al. |
| 2013/0010094 | A1 | 1/2013 | Satish et al. |
| 2013/0170729 | A1 | 7/2013 | Wardlaw et al. |
| 2013/0301901 | A1 | 11/2013 | Satish et al. |
| 2013/0303870 | A1 | 11/2013 | Satish et al. |
| 2013/0308852 | A1 | 11/2013 | Hamsici et al. |
| 2014/0079297 | A1 | 3/2014 | Tadayon et al. |
| 2014/0207091 | A1 | 7/2014 | Heagle et al. |
| 2014/0330094 | A1 | 11/2014 | Pacione et al. |
| 2015/0294460 | A1 | 10/2015 | Satish et al. |
| 2016/0027173 | A1 | 1/2016 | Satish et al. |

FOREIGN PATENT DOCUMENTS

| | | | |
|---|---|---|---|
| JP | S-59-161801 U | | 10/1984 |
| JP | S-62-144652 U | | 6/1987 |
| JP | H06510210 A | | 11/1994 |
| JP | H-11-37845 A | | 2/1999 |
| JP | 2002-331031 A | | 11/2002 |
| JP | 2003-075436 A | | 3/2003 |
| JP | 2005-052288 A | | 3/2005 |
| JP | 3701031 B2 | | 9/2005 |
| JP | 2006-280445 A | | 10/2006 |
| JP | 2008-055142 A | | 3/2008 |
| JP | 2011-515681 A | | 5/2011 |
| WO | 9217787 A1 | | 10/1992 |
| WO | 1996039927 A1 | | 12/1996 |
| WO | WO-2009/117652 A1 | | 9/2009 |
| WO | 2011019576 A1 | | 2/2011 |
| WO | 2013009709 A | | 1/2013 |
| WO | 2013172874 A | | 11/2013 |
| WO | 2013173356 A | | 11/2013 |

OTHER PUBLICATIONS

Aklilu, A. Gauss Surgical Measures Blood Loss with a Smartphone. Jun. 14, 2012. <http://www.health2con.com/news/2012/06/14/gauss-surgical-measures-blood-loss-with-a-smartphone/>.

Kamiyoshihara, M. et al. The Utility of an Autologous Blood Salvage System in Emergency Thoracotomy for a emothorax After Chest Trauma. Gen. Thorac. Cargiovasc. Surg. (2008); vol. 56, p. 222.

Pogorelc, D. iPads in the OR: New Mobile Platform to Monitor Blood Loss During Surgery. Jun. 6, 2012. <http://medcitynews.com/2012/06/ipads-in-the-or-new-mobile-platform-to-monitor-blood-loss-during-surgery/>.

Bellad, et al. "Standardized Visual Estimation of Blood Loss during Vaginal Delivery with its Correlation Hematocrit Changes—A Descriptive Study." South Asian Federation of Obstetrics and Gynecology 1.1 (2009): 29-34. Web.

ACOG (2012). "Optimizing protocols in obstetrics," Series 2, 25 total pages.

Adkins, A.R. et al. (2014). "Accuracy of blood loss estimations among anesthesia providers," *AANA Journal* 82(4):300-306.

Al-Kadri, H.M. et al. (2014). "Effect of education and clinical assessment on the accuracy of post partum blood loss estimation," *BMC Preg. Childbirth* 14:110, 7 total pages.

AWHONN Practice Brief (2014). "Quantification of blood loss: AWHONN practice brief number 1," *AWHONN* p. 1-3.

Bose, P. et al. (2006). "Improving the accuracy of estimated blood loss at obstetric haemorrhage using clinical reconstructions," *BJOG* 113(8):919-924.

Eipe, N. et al. (2006). "Perioperative blood loss assessment—How accurate?" *Indian J. Anaesth.* 50(1):35-38.

Extended European Search Report dated Apr. 1, 2015, for EP Application No. 12 810 640.8, filed on Jul. 9, 2012, 8 pages.

Extended European Search Report dated Nov. 23, 2015, for EP Application No. 13 790 688.9, filed on May 14, 2013, 9 pages.

Extended European Search Report dated Nov. 17, 2015, for EP Application No. 13 790 449.6, filed on Jan. 10, 2013, 8 pages.

Final Office Action dated Feb. 12, 2016, for U.S. Appl. No. 13/544,664, filed Jul. 9, 2012, 9 pages.

Final Office Action dated Jul. 26, 2016, for U.S. Appl. No. 14/876,628, filed Oct. 6, 2015, 5 pages.

Habak, P.J. et al. (2016). "A comparison of visual estimate versus calculated estimate of blood loss at vaginal delivery," *British J. Med. Medical Res.* 11(4):1-7.

Holmes, A.A. et al. (2014). "Clinical evaluation of a novel system for monitoring surgical hemoglobin loss," *Anesth. Analg.* 119(3):588-594.

International Search Report dated Sep. 17, 2012, for PCT Application No. PCT/US2012/045969, filed on Jul. 9, 2012, 2 pages.

International Search Report dated Sep. 24, 2013, for PCT Application No. PCT/US2013/040976, filed on May 14, 2013, 2 pages.

International Search Report dated Mar. 26, 2013, for PCT Application No. PCT/US2013/021075, filed on Jan. 10, 2013, 2 pages.

International Search Report dated Jul. 24, 2015, for PCT Application No. PCT/US2015/026036, filed on Apr. 15, 2015, 2 pages.

Jones, R. (2015). "Quantitative measurement of blood loss during delivery," *AWHONN* p. S41.

Lyndon, A. et al. (2010). "Blood loss: Clinical techniques for ongoing quantitative measurement," *CMQCC Obstetric Hemorrhage Toolkit*, pp. 1-7.

Lyndon, A. et al. (2015). "Cumulative quantitative assessment of blood loss," *CMQCC Obstetric Hemorrhage Toolkit Version 2.0*, pp. 80-85.

Manikandan, D. et al. (2015). "Measurement of blood loss during adenotonsillectomy in children and factors affecting it," *Case Reports in Clinical Medicine* 4:151-156.

Merck for Mother's Program (2012). Blood loss measurement: Technology opportunity assessment, 9 total pages.

Non-Final Office Action dated Aug. 13, 2015, for U.S. Appl. No. 13/544,664, filed Jul. 9, 2012, 8 pages.

Non-Final Office Action dated Aug. 2, 2016, for U.S. Appl. No. 13/544,664, filed Jul. 9, 2012, 6 pages.

Non-Final Office Action dated May 9, 2014, for U.S. Appl. No. 13/544,679, filed Jul. 9, 2012, 7 pages.

Non-Final Office Action dated Sep. 5, 2014, for U.S. Appl. No. 13/738,919, filed Jan. 10, 2013, 8 pages.

Non-Final Office Action dated Mar. 20, 2015, for U.S. Appl. No. 14/613,807, filed Feb. 4, 2015, 8 pages.

Non-Final Office Action dated Dec. 15, 2015, for U.S. Appl. No. 14/876,628, filed Oct. 6, 2015, 8 pages.

Notice of Allowance dated May 12, 2014, for U.S. Appl. No. 13/544,646, filed Jul. 9, 2012, 10 pages.

Notice of Allowance dated Sep. 3, 2014, for U.S. Appl. No. 13/544,679, filed Jul. 9. 2012. 8 pages.

Notice of Allowance dated Nov. 10, 2014, for U.S. Appl. No. 13/738,919, filed Jan. 10, 2013, 10 pages.

Notice of Allowance dated Jun. 25, 2015, for U.S. Appl. No. 14/613,807, filed Feb. 4. 2015, 10 pages.

Notice of Allowance dated Oct. 26, 2016, for U.S. Appl. No. 14/876,628, filed Oct. 6, 2015, 11 pages.

Roston, A.B. et al. (2012). "Chapter 9: Blood loss: Accuracy of visual estimation," in *A comprehensive textbook of postpartum hemorrhage: An essential clinical reference for effective management*, $2^{nd}$ edition, Sapiens publishing, pp. 71-72.

Schorn, M.N. (2010). "Measurement of blood loss: Review of the literature," *J. Midwifery and Women's Health* 55(1):20-27.

Sukprasert, M. et al. (2006). "Increase accuracy of visual estimation of blood loss from education programme," *J. Med. Assoc. Thai* 89(suppl. 4):S54-S59.

Written Opinion of the International Searching Authority dated Sep. 17, 2012, for PCT Application No. PCT/US2012/045969, filed on Jul. 9, 2012, 4 pages.

(56) References Cited

OTHER PUBLICATIONS

Written Opinion of the International Searching Authority dated Sep. 24, 2013, for PCT Application No. PCT/US2013/040976, filed on May 14, 2013, 4 pages.
Written Opinion of the International Searching Authority dated Mar. 26, 2013, for PCT Application No. PCT/US2013/021075, filed on Jan. 10, 2013, 6 pages.
Written Opinion of the International Searching Authority dated Jul. 24, 2015, for PCT Application No. PCT/US2015/026036, filed on Apr. 15, 2015, 6 pages.
Notice of Allowance dated Feb. 15, 2017, for U.S. Appl. No. 13/544,664, filed Jul. 9, 2012, 10 pages.

* cited by examiner

SYSTEM AND METHODS FOR MANAGING BLOOD LOSS OF A PATIENT

CROSS-REFERENCE TO RELATED APPLICATIONS

This application also claims the benefit of U.S. Provisional Patent Application No. 61/776,577, filed on 11 Mar. 2013, U.S. Provisional Patent Application No. 61/646,822, filed on 14 May 2012, and U.S. Provisional Patent Application No. 61/722,780, filed on 5 Nov. 2012, all of which are incorporated herein in their entireties by this reference.

This application is related to U.S. patent application Ser. No. 13/544,646, filed on 9 Jul. 2012, and to U.S. patent application Ser. No. 13/738,919, filed on 10 Jan. 2013, both of which are incorporated herein in their entireties by this reference.

TECHNICAL FIELD

This invention relates generally to the surgical field, and more specifically to a new and useful system and method for managing blood loss of a patient for use in surgical practice.

BACKGROUND

Overestimation and underestimation of patient blood loss is a significant contributor to high operating and surgical costs for hospitals, clinics and other medical facilities. Specifically, overestimation of patient blood loss results in wasted transfusion-grade blood and higher operating costs for medical institutions and can lead to blood shortages. Underestimation of patient blood loss is a key contributor of delayed resuscitation and transfusion in the event of hemorrhage and has been associated with billions of dollars in avoidable patient infections, re-hospitalizations, and lawsuits annually. Uninformed estimation of varying patient hematocrit during hemorrhage, blood transfusion, and intravenous saline infusion further exacerbates inaccurate estimation of patient red blood cell loss and negatively impacts the timing and quantity of fluids supplied to a patient intravenously. Thus, there is a need in the surgical field for a new and useful system and method for managing blood loss of a patient. This invention provides such a new and useful system and method.

DESCRIPTION OF THE PREFERRED EMBODIMENTS

The following description of preferred embodiments of the invention is not intended to limit the invention to these preferred embodiments, but rather to enable any person skilled in the art to make and use this invention.

1. First Method

Figure 1:
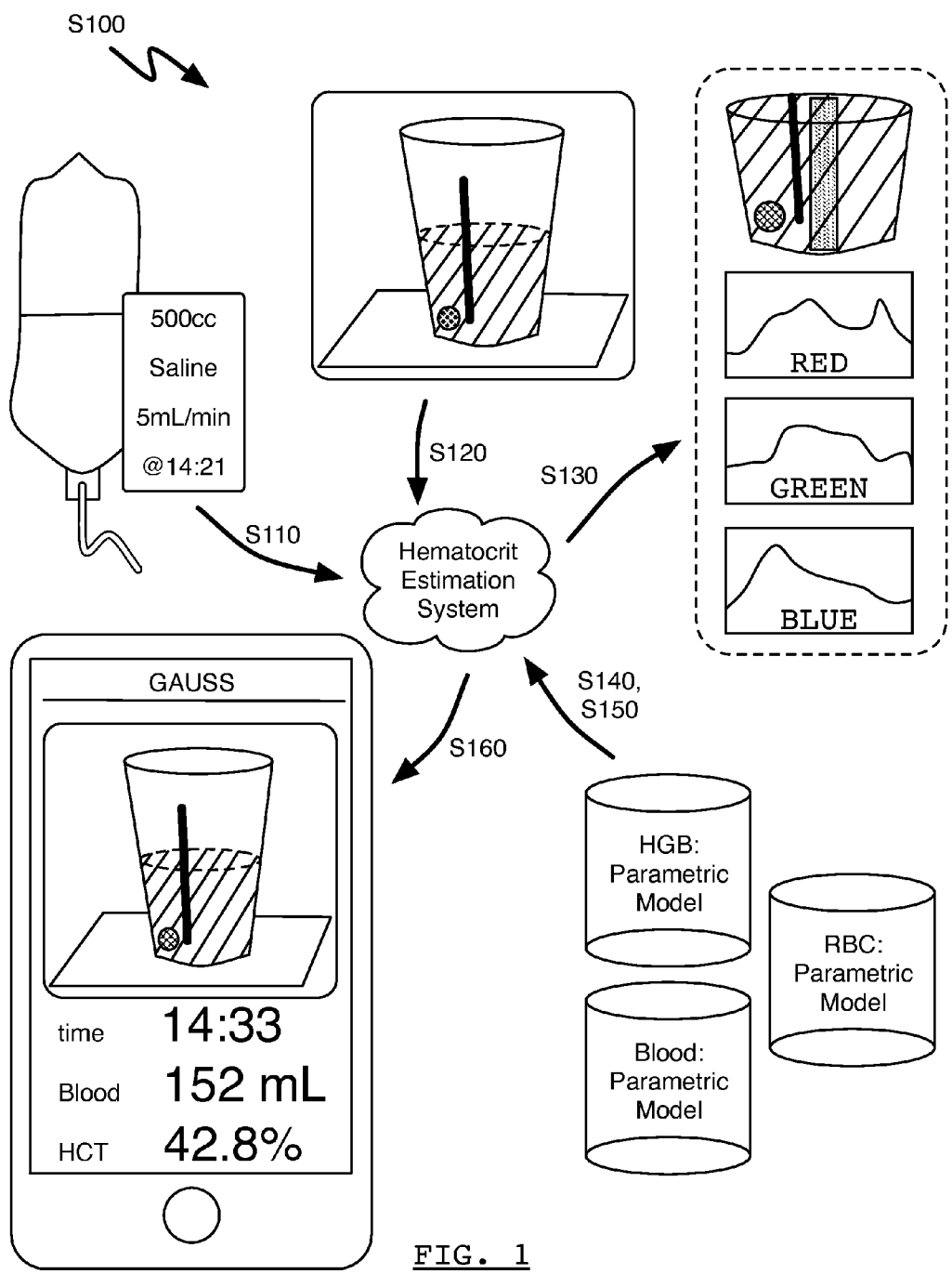
FIG. 1 is a flowchart representation of a first method.

As shown in FIG. 1, method S100 for managing blood loss of a patient includes: tracking a quantity of a fluid administered to the patient intravenously in Block S110; receiving an image of a physical sample in Block S120; extracting a feature from an area of the image correlated with the physical sample in Block S130; estimating a red blood cell content of the physical sample based on the extracted feature in Block S140; estimating an extracorporeal blood content of the physical sample based on the estimated red blood cell content of the physical sample in Block S150; and estimating a hematocrit of the patient based on a previous hematocrit of the patient, the quantity of the fluid administered to the patient, and the estimated extracorporeal blood content of the physical sample in Block S160.

Figure 2:
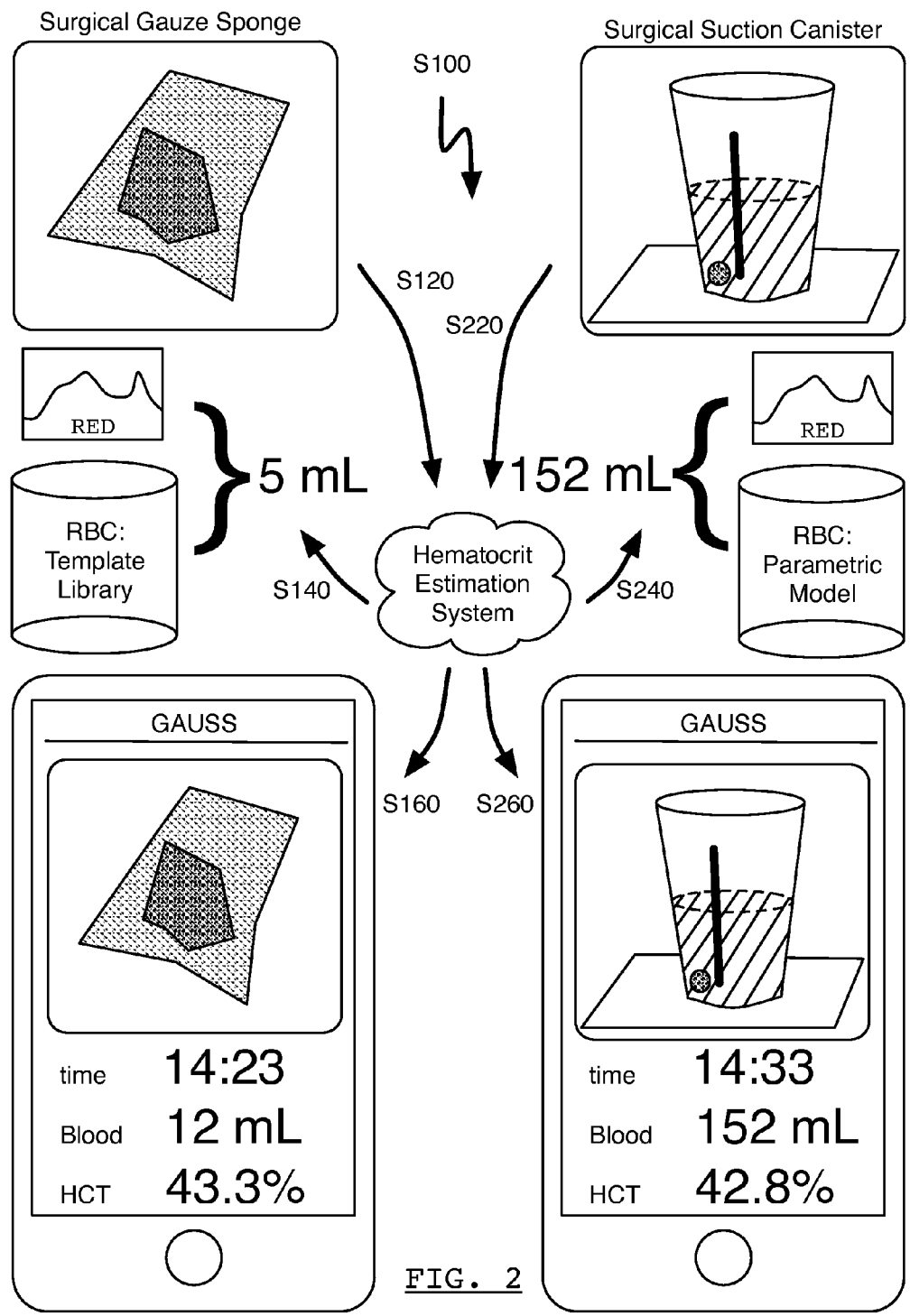
FIG. 2 is a flowchart representation of one variation of the first method.

As shown in FIG. 2, one variation of first method S100 for managing blood loss of a patient includes: receiving an image of a first physical sample at a first time in Block S120; estimating a first red blood cell content of the first physical sample based on a feature extracted from the image of the first physical sample in Block S140; estimating an intravascular hematocrit of the patient substantially current to the first time based on an initial intravascular hematocrit of the patient, the estimated first red blood cell content of the first physical sample, and a quantity of fluid administered to the patient intravenously up to the first time in Block S160; receiving an image of a second physical sample at a second time in Block S220; estimating a second red blood cell content of the second physical sample based on a feature extracted from the image of the second physical sample in Block S240; and estimating an intravascular hematocrit of the patient substantially current to the second time based on the estimated intravascular hematocrit of the patient substantially current to the first time, the estimated second red blood cell content of the second physical sample, and a quantity of fluid administered to the patient, and the estimated extracorporeal blood content of the physical sample in Block S260.

Hematocrit (HCT) (packed cell volume (PCV), erythrocyte volume fraction (EVF)) is the volume percentage of red blood cells in blood and is related to intravascular red blood cell count (RBC) and plasma volume (PV) according to the formula:

$$HCT = \frac{RBC}{VB} = \frac{RBC}{RBC + PV}$$

wherein the total volume of blood (VB) is the sum of RBC and PV. Hemoglobin is the primary oxygen-transport metalloprotein in blood and makes up most (e.g., 98%) of the dry-weight of a red blood cell. Hematocrit is therefore a fundamental indicator of the oxygen-carrying capacity of blood and can be indicative patient fluid needs, such as intravenous infusion or transfusion of saline, blood, plasma, red blood cells in solution, etc.

Generally, first method S100 functions to estimate the intravascular hematocrit of a patient based on fluids lost by and fluids administered to the patient over time. First method S100 implements machine vision techniques to analyze images of physical samples, such as a surgical gauze sponge, a surgical towel, a surgical dressing, a surgical suction canister, a cell salvage canister, or a surgical drape, to estimate the quantity or volume of red blood cells (and therefore blood) lost by the patient. First method S100 also tracks intravenous administration of fluids, such as crystalloids (e.g., saline) or colloids (e.g., blood or blood components), over time, thereby maintaining a substantially current estimate of patient hematocrit based on fluids lost from and added to the patient's circulatory system over time. First method S100 can further account for other variables in estimating a current intravascular hematocrit of the patient, such as an initial known or estimated intravascular hematocrit, an estimated extracorporeal red blood cell mass or volume, an estimated extracorporeal hemoglobin mass or volume, and/or any intravenous fluid infusions or transfusions provided to the patient. Generally, by accounting for any of these variables over time, first method S100 can maintain a substantially reliable estimate of patient intravascular hematocrit.

During a medical event, blood loss reduces intravascular blood volume, and, to compensate, patients are often initially administered a saline drip or other intravenous non-blood (i.e., crystalloid) fluid to boost intravascular fluid volume. However, as the blood of the patient is diluted with saline or other non-blood-based fluid, the oxygen-carrying capacity of the patient's circulatory system diminishes, as indicated by reduced patient hematocrit. Patient risk increases with reduced blood volume and/or reduced red blood cell count per volume of blood, and first method S100 can therefore be useful in a hospital, medical clinic, or other medical facility or setting to track and maintain patient intravascular hematocrit. For example, first method S100 can be applicable in a surgical setting or during a childbirth in which a patient bleeds, wherein saline is administered to the patient to maintain intravascular (e.g., intravenous) volume and wherein a blood component (e.g., red blood cells) is subsequently administered to prevent excessive loss of intravascular oxygen-carrying capacity. First method S100 can therefore track the patient's intravascular fluid flux to maintain a current estimate of the patient's hematocrit, thereby enabling a user (e.g., a surgeon, anesthesiologist, nurse) to avoid over- and under-administration of fluids that could otherwise lead to hypovolemia, hypervolemia, and/or related complications.

First method S100 can additionally or alternatively function to estimate total blood, red blood cell, or hemoglobin loss of the patient over time, to detect the presence of blood in a sample (e.g., surgical gauze sponge, a surgical suction canister), to compute blood spread rate, to calculate blood surface area, to estimate patient risk level (e.g., hypovolemic shock), to determine patient hemorrhage classification, to provide warnings, to suggest administration of or automatically administer necessary fluids intravenously (e.g., blood, saline), or to provide any other functionality.

As shown in FIGS. 1 and 2, first method S100 can be implemented by a computer system as a hematocrit estimation system that receives transfusion and/or infusion data, analyzes photographic images of bloodied samples to estimate patient blood loss, and updates an estimated patient hematocrit according to the transfusion/infusion data, the estimated patient blood loss, and/or other related information. The computer system can be cloud-based (e.g., Amazon EC3), a mainframe computer system, a grid-computer system, or any other suitable computer system. First method S100 can be implemented by a handheld (i.e., mobile) computing device, such by a smartphone, digital music player, or tablet computer executing a native hematocrit estimation application, such as shown in FIG. 2. For example, a camera integral with the computing device can capture an image of the physical sample, and a processor integral within the computing device can implement Blocks S110, S120, S130, etc. Additionally or alternatively, the computing device can communicate with a remote server, such as over the Internet via a wireless connection, wherein the server performs at least some Blocks of first method S100 and wherein at least some of the outputs of first method S100 are transmitted back to the computing device for further analysis and/or subsequent release to a user. The computing device can also include or be coupled to a digital display such that first method S100 can display information to a user (e.g., a nurse or anesthesiologist) through the display. For example, a display integral with the computing device can display the estimated intravascular hematocrit, an estimated total patient blood loss, a hypovolemia or hypovolemia warning, a suggestion to administer a particular fluid intravenously, or any other relevant information. However, first method S100 can be implemented in or by any other computing device, system, or combination thereof.

Figure 3:
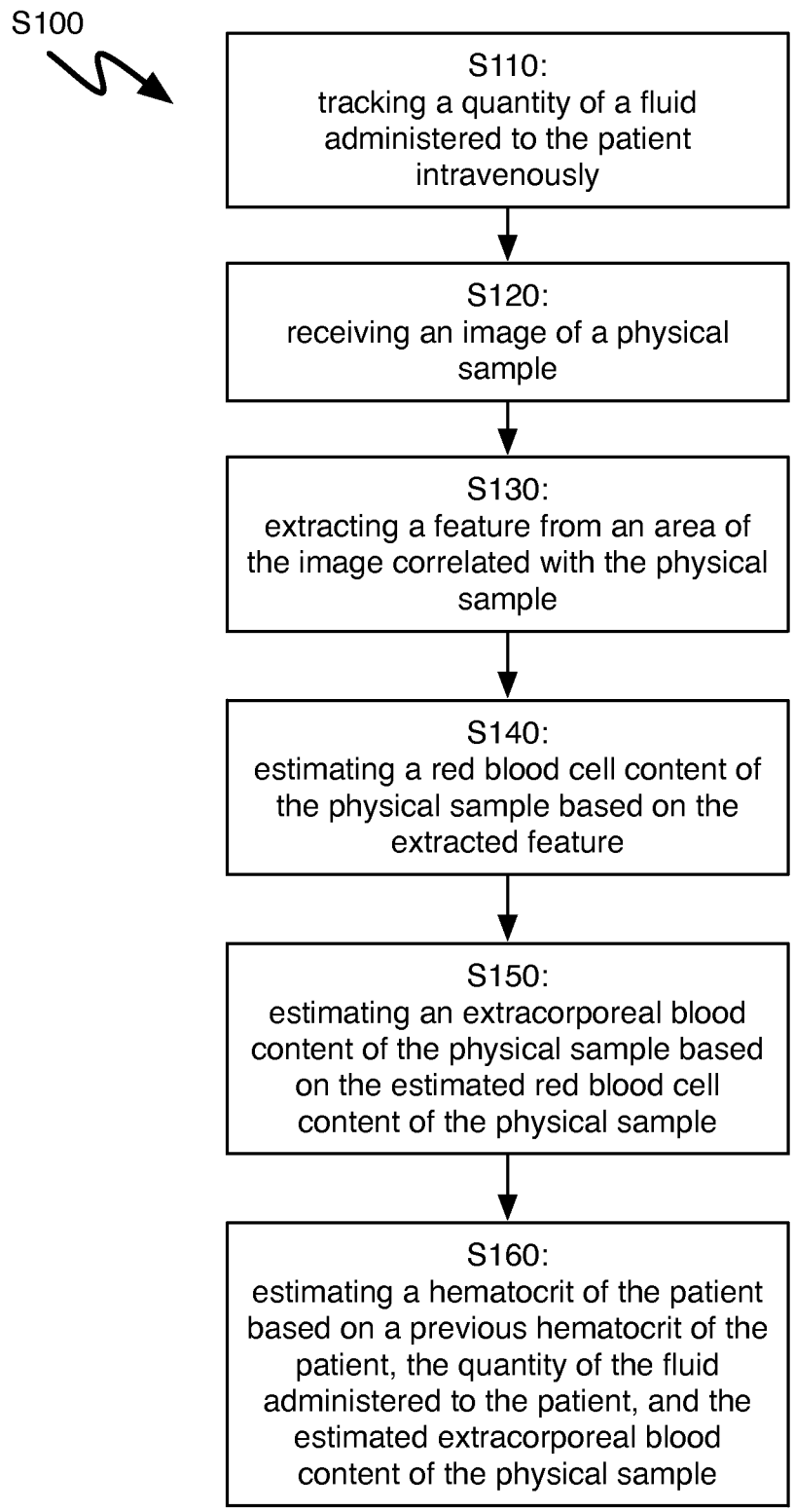
FIG. 3 is a flowchart representation of the first method.

As shown in FIG. 3, Block S110 of first method S100 recites tracking a quantity of a fluid administered to the patient intravenously. Generally, Block S110 functions to collect time-dependent data pertaining to patient blood, saline, and/or other infusions and/or transfusions, which can enable first method S100 to estimate changes in the volume and composition of fluid in the patient's circulatory system when coupled with data pertaining to the contents of infused and/or transfused fluids. Block S110 can therefore track administration of crystalloids (e.g., saline), colloids (e.g., blood), and/or other fluids, whether administered exclusively or simultaneously.

Block S110 can monitor intravenous administration of fluid(s) by recording an initial time of administration of the fluid and tracking the quantity of the fluid administered to the patient according to a transfusion rate. In one example implementation, the computer system implementing first method S100 can include an interface through which a user can enter data related to a fluid infusion or transfusion. In this example implementation, the interface can guide the user to enter the type of fluid (e.g., saline, plasma, red blood cells, whole blood), a fluid flow rate (e.g., 100 mL/min of warmed blood), a transfusion or infusion start time, and/or an initial fluid volume in an IV bag, as shown in FIG. 1. By integrating the flow rate over time up to the total initial volume of the IV bag, Block S110 can track the volume of fluid intravenously administered to the patient via the IV bag. In this example implementation, Block S110 can therefore track one or more fluids administered to the patient substantially indirectly.

In another example implementation, the computer system implementing first method S100 can include a flow sensor coupled to an IV line, wherein Block S110 monitors the volume of fluid administered to the patient based on an output of the flow sensor. For example, the flow sensor can be an optical flow sensor arranged over a metering block at the outlet of an IV bag. Therefore, in this example implementation, Block S110 can track one or more fluids administered to the patient substantially directly.

Block S110 can also receive data pertaining to the contents (i.e., composition) of infused or transfused fluid, such as through the interface of the computer system described above. Alternatively, Block S110 can implement machine vision to determine the contents of an IV bag, as described in U.S. Provisional Patent Application No. 61/722,780 and U.S. patent application Ser. No. 13/544,646.

In one example implementation, Block S110 further interfaces with an optical sensor to capture an image of an IV bag, such as an allogeneic blood transfusion bag, a blood component (e.g., plasma, red blood cell) bag, or a saline therapy IV bag, and analyzes the image of the IV bag to estimate the composition of fluid therein. For example, Block S110 can receive a second image of the blood transfusion bag, extract a color-related feature from an area of the second image correlated with the blood transfusion bag, and estimate a red blood cell content of the blood transfusion bag based on the color-related feature. In this example, Block S110 can implement a parametric or non-parametric model to correlate the extracted (color) feature with a red blood cell concentration, as described in U.S. patent application Ser. Nos. 13/544,646 and 13/738,919. Block S110 can further implement machine vision techniques, such as edge detection and/or template matching, to determine the type of IV bag, the level of fluid in the IV bag, and thus the volume of fluid in the IV bag. From this data, Block S110 can estimate the red blood cell count, plasma volume, and/or hematocrit of blood in the IV bag.

In the forgoing example implementation, Block S110 can further implement machine vision techniques to determine the type of bag in the image. For example, Block S110 can identify a bag with a rectangular perimeter as a blood transfusion bag and can identify a bag with a circular perimeter as a urethral catheter bag, wherein the blood transfusion bag is marked as containing fluid flowing into the patient and the urethral catheter bag is marked as containing fluid flowing out of the patient.

Alternatively, Block S110 can implement machine vision to scan a barcode, printed or embossed text, or handwritten text on the bag to identify the type and/or contents of the bag. In an example in which the bag is a blood transfusion bag, Block S110 can read a barcode on a sticker on the bag, access a database including the barcode, and retrieve bag type and/or content-related information from the database based on the barcode. In this example, first method S100 can thus also log entry of the blood transfusion bag into the operating room, check the blood type within the bag against the patient's blood type, capture an initial infusion time, and/or track blood inventory in an operating or delivery room.

Therefore, Block S110 can track intravenous administration of a crystalloid fluid, a colloid fluid, or any other suitable fluid. Block S110 can also receive the composition of an administered fluid, such as from a nurse or anesthesiologist, determine the composition of administered fluid directly by analyzing an image of the fluid, or determine the composition of administered fluid indirectly by accessing IV bag data, such as from a remote server or database. However, Block S110 can function in any other way to track a quantity of a fluid administered to the patient intravenously.

As shown in FIG. 3, Block S120 of first method S100 recites receiving an image of a physical sample. As described above and shown in FIG. 4, Block S120 can similarly recite receiving a first image of a first physical sample at a first time, and Block S240 can recite receiving a second image of a second physical sample at a second time. Generally, Block S120 functions to collect an image of the physical sample at a known time (e.g., the first time) and/or to collect an image of the physical sample with a known time of use of the physical sample. Block S220 similarly functions to collect a second image of a second physical sample at a later time (e.g., the second time) such that Block S160 and Block S260 can generate updated hematocrit estimates over time. The (first) physical sample (and second physical sample) can be any of a surgical gauze sponge, a surgical towel, a surgical dressing, a surgical suction canister, a cell salvage canister, or any other absorbent textile or vessel used to collect blood or other bodily fluids during a surgery, delivery, or other medical event. However, the physical sample can additionally or alternatively be a droplet, drop, or pool of blood on a ground, table, wall, or floor surface, a piece of clothing, an external skin surface, a surgical glove, a surgical implement or tool, or any other surface, material, or object. The image of the physical sample can be a static, single-frame image including at least a portion of the physical sample, a multi-frame video feed including multiple static images of the fluid canister, a color image, a black and white image, a grayscale image, an infrared image, a field of view of an optical sensor, a fingerprint of a field of view of an optical sensor, a point cloud, or any other suitable type of image. The image can be captured by an optical sensor, such as a digital color camera, an RGB camera, or any number of charge-coupled device (CCD) sensors, complimentary metal-oxide-semiconductor (CMOS) active pixel sensors, or any other optical sensor of any other type. For example, the optical sensor can be arranged within a handheld computing device implementing first method S100, adjacent an operating table, or over a delivery table.

Figure 5:
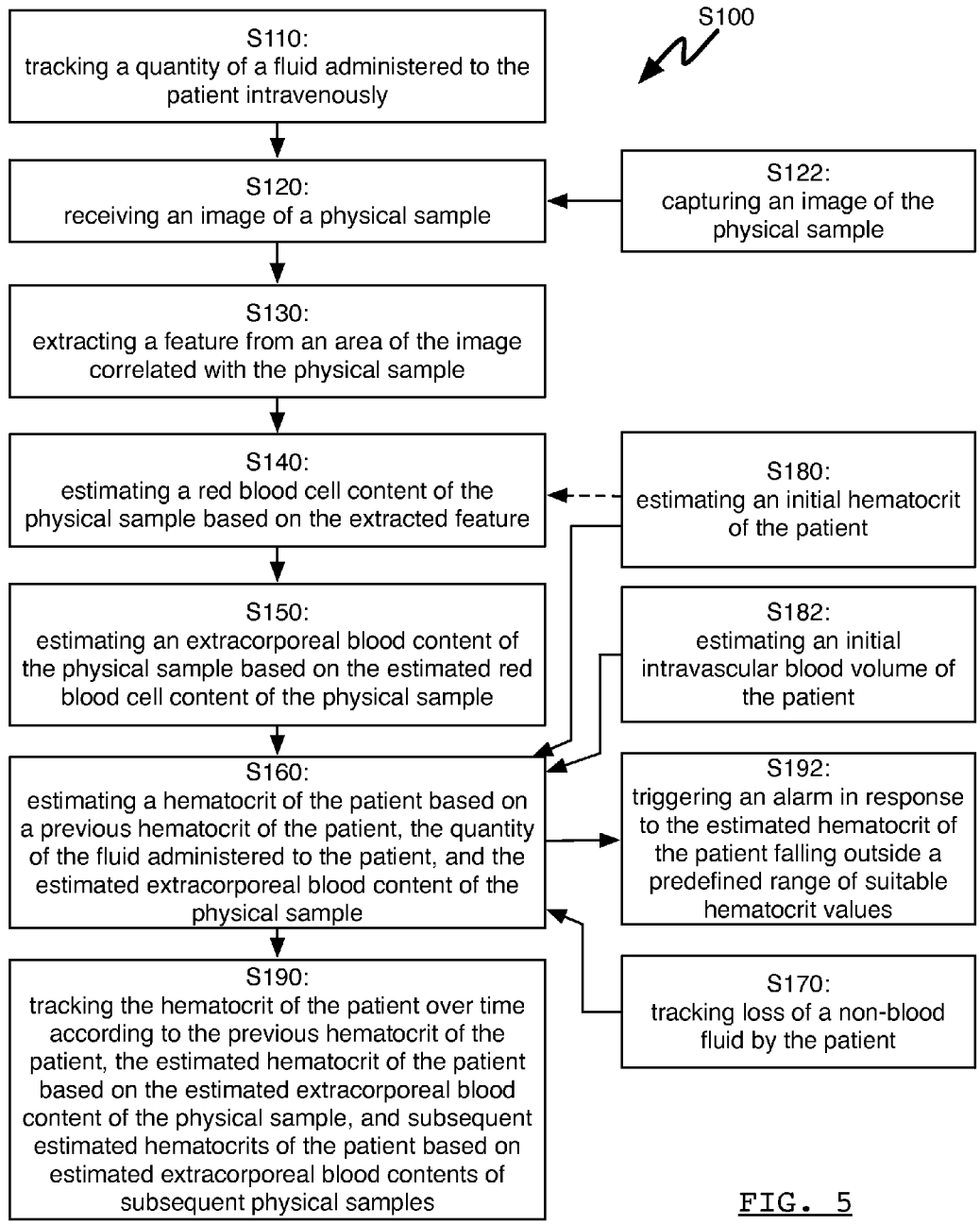
FIG. 5 is a flowchart representation of one variation of the first method.

As shown in FIG. 5, one variation of first method S100 includes Block S122, which recites capturing the image of the physical sample. Block S122 can interface with a camera or other suitable optical sensor to capture the image of a field of view of the camera or optical sensor, wherein the physical sample is in the field of view of the camera or optical sensor. Block S122 can capture the image that is a static, single-frame image including at least a portion of the physical sample. Alternatively, Block S122 can capture the image that is a multi-frame video feed including multiple static images of the fluid canister.

As described in U.S. patent application Ser. No. 13/738,919, in one implementation in which the physical sample is a suction canister, a cell salvage canister, or other vessel, Block S122 can capture the image of the vessel according to a time schedule, such as every thirty seconds or every two minutes. Alternatively, Block S122 can implement machine vision and/or machine recognition techniques to identify the vessel within the field of view of the optical sensor and trigger image capture once a vessel is detected. For example, Block S122 can capture an image of the field of view of the optical sensor each time a user holds the camera (e.g., the computing device that incorporates the camera) up to the vessel. Similarly, Block S122 can capture the image of the physical sample once a threshold increase in the fluid volume of the vessel is detected. Therefore, Block S122 can capture images of the physical sample automatically, such as based on a timer, changes in fluid volume of the vessel, or availability of the vessel for imaging, which can enable first method S100 to track fluid collection in the vessel over time.

As described in U.S. patent application Ser. No. 13/544,646, in one implementation in which the physical sample is a surgical sponge gauze, Block S122 can implement machine vision and/or machine recognition techniques to identify the surgical sponge gauze in the field of view of the optical sensor and automatically capture the image of the surgical sponge gauze. Alternatively, in the foregoing implementations, Block S122 can capture the image of the physical sample according to a manual input, such as from a nurse or anesthesiologist.

Block S122 can also timestamp the image of the physical sample, such as based on when the image was captured, when the physical sample that is a surgical sponge gauze was used, and/or when the physical sample that is a fluid suction canister was filled, replaced, and/or emptied. Block S122 can thus enable first method S100 to track changes in both the patient's intravascular fluid volume and hematocrit based on a series of subsequent images, wherein an extracorporeal blood volume estimate for each image can be based on both an estimated red blood cell content of the physical sample in a particular image and a hematocrit estimated for a time approximately the same as that noted in the timestamp of the particular image. However, Block S122 can function in any other way to capture the image of the physical sample. Block S122 can also capture the second image of the second physical sample, as shown in FIG. 2.

Block S130 of first method S100 recites extracting a feature from an area of the image correlated with the physical sample. Generally, Block S130 functions to identify and select a portion of the image that is indicative of the hemoglobin mass (or red blood cell content, red blood cell count, red blood cell volume, red blood cell mass, etc.) of the physical sample. In one example implementation, because red blood cells are red, Block S130 extracts the portion of the image by isolating a substantially red region of the image. In another example implementation, Block S130 implements object recognition to identity the physical sample in the image and to remove a background from the image. For example, Block S130 can implement object localization, segmentation (e.g., edge detection, background subtraction, grab-cut-based algorithms, etc.), gauging, clustering, pattern recognition, template matching, feature extraction, descriptor extraction (e.g., extraction of texton maps, color histograms, HOG, SIFT, etc.), feature dimensionality reduction (e.g., PCA, K-Means, linear discriminant analysis, etc.), feature selection, thresholding, positioning, color analysis, parametric regression, non-parametric regression, unsupervised or semi-supervised parametric or non-parametric regression, or any other type of machine learning and/or machine vision technique to select the representative area of the image. Block S130 can further identify the type of physical sample and/or estimate a physical dimension of the physical sample based on the selected area.

Figure 6A:
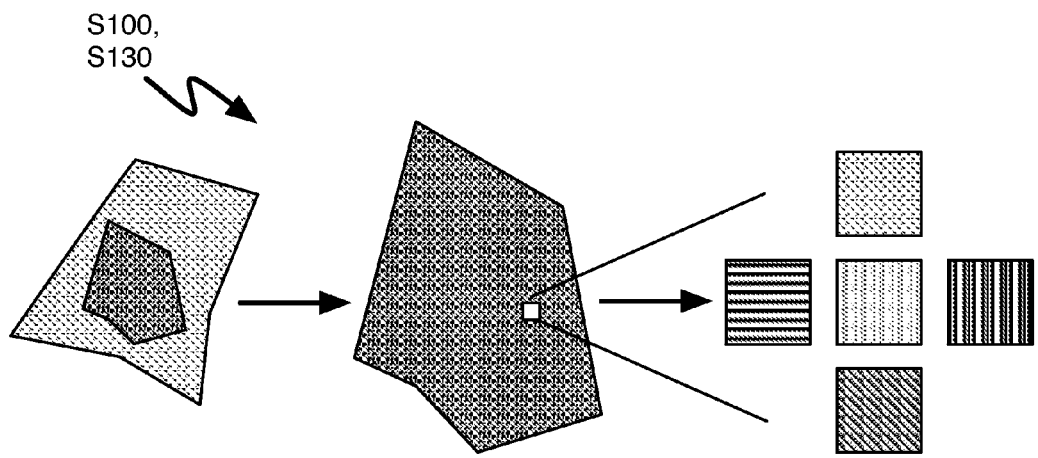
FIGS. 6A and 6B area schematic representations in accordance with one variation of the first method.
Figure 6B:
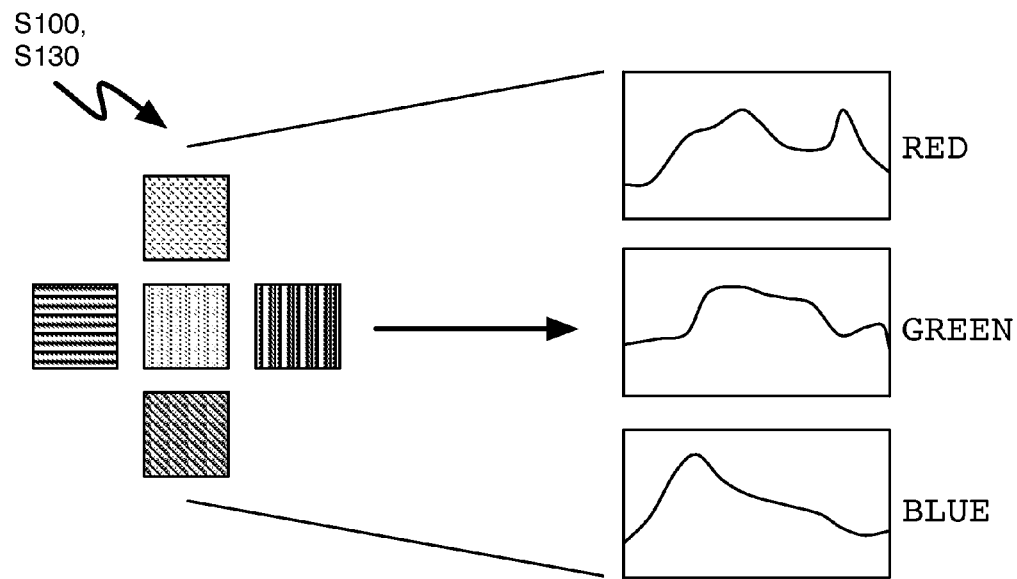

Block S130 can extract the feature, from one or more pixels of the image, that is a color (red), a color intensity (e.g., redness value), a luminosity, a hue, a saturation value, a brightness value, a gloss value, or other color-related value in one or more component spaces, such as the red, blue, green, cyan, magenta, yellow, key, and/or Lab component spaces. Block S130 can alternatively extract the feature that is a numerical color identifier, such as a HEX code value (e.g., #FF0000, #A00000, #880000, etc.) or an RGB code value (e.g., (255, 0, 0), (160, 0, 0), (190, 0, 0), etc.). Block S130 can also extract one or more features that is a histogram of various color or color-related values in a set of pixels within the image. As shown in FIGS. 6A and 6B, Block S130 can also extract the feature that is a cluster of pixels within the selected area and correlated with a portion of the physical sample than contains blood, such as a cluster of pixels that can be compared to template images in a library of template images of known red blood cell content. However, Block S130 can extract any other suitable feature from one or more pixels within the image.

In one example implementation, Block S130 extracts a color intensity value of a set of pixels within an area of the image correlated with the physical sample such that Block S140 can estimate the red blood cell content of the physical sample by implementing a parametric model to transform the color intensity value into a quantity of red blood cells in the physical sample. In another example implementation, Block S130 extracts a subset of pixels from a set of pixels within an area of the image correlated with the physical sample such that Block S140 can estimate the red blood cell content of the physical sample by matching the subset of pixels with a template image in a library of template images of known red blood cell content, as described in U.S. patent application Ser. No. 13/544,646.

Therefore, as shown in FIGS. 6A and 6B, Block S130 can extract features from multiple pixels within the image to amass a set of features indicative of fluid quality over an area of the image correlated with the physical sample or a portion of the physical sample that contains blood. For example, Block S130 can segment a portion of the image into m-pixel by n-pixel clusters of pixels, wherein an o by p array of pixel clusters substantially fills a selected area of the image. Block S130 can then analyze each pixel cluster to extract one feature per pixel cluster. Block S130 can further average or otherwise combine features from the pixel clusters to extract a single feature indicative of the composition of the physical sample from the image. In another example, Block S130 can segment the selected area into non-overlapping single-pixel-thickness (horizontal) rows extending across the full width of an area of the image correlated with the physical sample. In this example, Block S130 can average pixel properties in each row of pixels to extract a single feature from each row. Similarly, Block S130 can segment the selected area into three-pixel-thickness row sets extending across the full width of a selected area of the image, wherein the outer single rows of each row set (except the lowermost and uppermost row sets) are shared with adjacent row sets, and wherein the pixels in each row set are averaged to extract a single feature from a set of pixels. Block S130 can additionally or alternatively segment the selected area into non-overlapping triangular pixel clusters, overlapping cross-shaped five-pixel arrays (shown in FIGS. 6A and 6B), overlapping circular pixel clusters, or any other suitable shape and number of overlapping and/or discrete pixel clusters and, from these pixel clusters, extract one or more of the same or different types of features from the set of pixels. Block S130 can alternatively extract a feature from each individual pixel in the selected area or extract any other number of features in any other way from information stored in pixels of the image bounded by an area of the image correlated with the physical sample.

Therefore, Block S130 can extract from the image one or more features indicative of red blood cell content of the physical sample, such as described in U.S. patent application Ser. No. 13/544,646. However, Block S130 can function in any other way to extract a feature of any other suitable type or format from an area of the image correlated with the physical sample. Block S130 can also extract a feature of any suitable type or format from an area of the second image correlated with the second physical sample.

Figure 4:
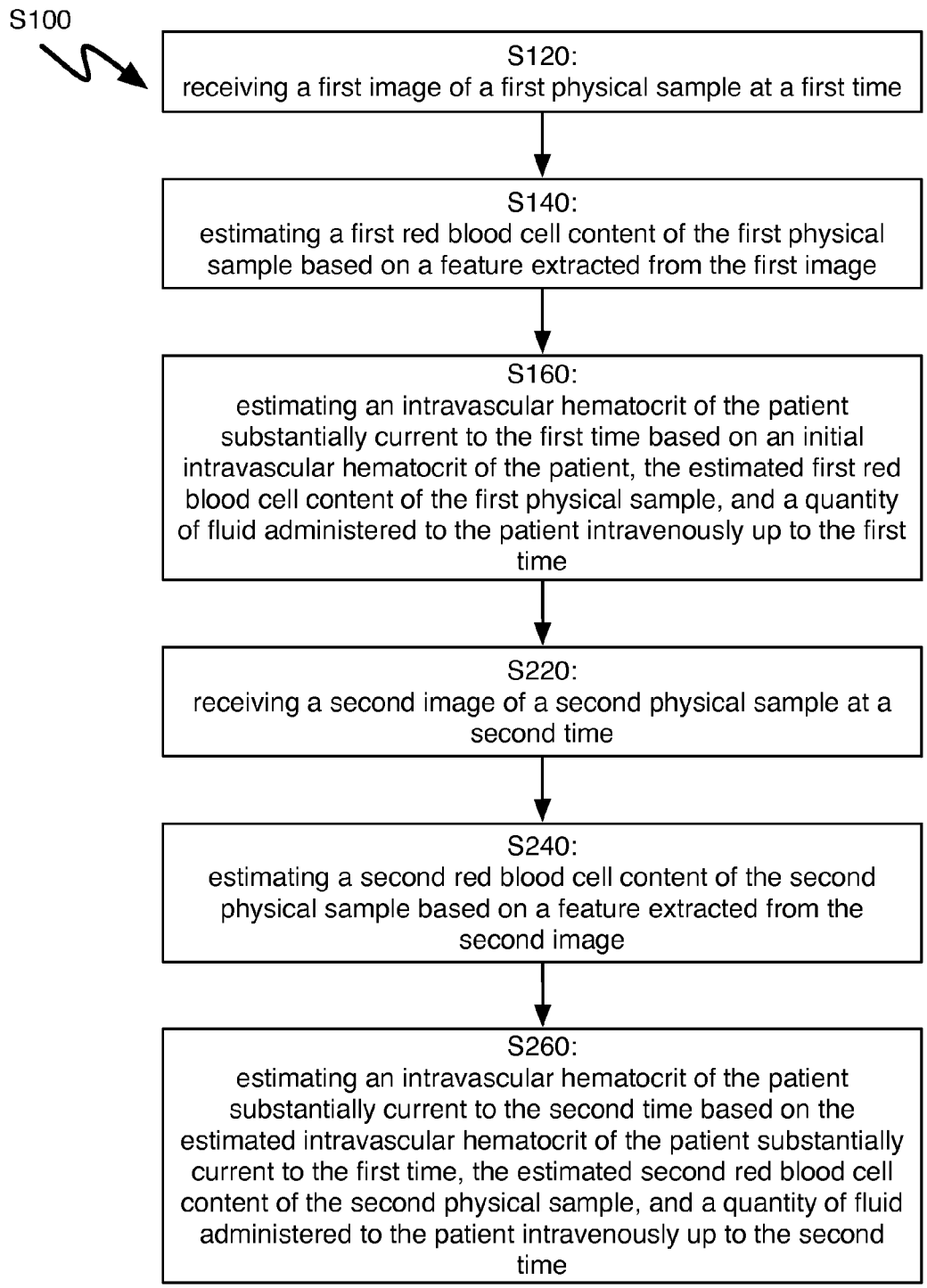
FIG. 4 is a flowchart representation of one variation of the first method.

As shown in FIG. 3, Block S140 of first method S100 recites estimating a red blood cell content of the physical sample based on the extracted feature. As shown in FIG. 4, Block S240 can similarly recite estimating a second red blood cell content of the second physical sample based on a feature extracted from the second image. Generally, Block S140 functions to transform one or more features extracted from the image extracted in Block S130 into an estimate of the red blood cell content of the physical sample. For example, Block S140 can implement parametric analysis techniques and/or non-parametric analysis techniques, such as described in U.S. patent application Ser. No. 13/544,646, to estimate the red blood cell content of the physical sample.

In one implementation, Block S130 extracts features from pixel clusters in the image, and Block S140 tags each pixel cluster with a red blood cell content based on a non-parametric correlation of each pixel cluster with a template image in a library of template images of known red blood cell contents. For example, Block S130 can extract a color intensity in the red component space from a set of pixel clusters, and Block S140 can implement a K-nearest neighbor method to compare each extracted feature with redness intensity values of template images. In this example, each template image can include a pixel cluster tagged with a known fluid quality, such as hemoglobin or red blood cell volume or mass per pixel unit (e.g., hemoglobin or red blood concentration). Once a suitable match between a particular pixel cluster and a particular template image is found, Block S140 can project known red blood cell information from the particular template image onto the particular pixel cluster. Block S140 can then aggregate, average, and/or otherwise combine pixel cluster tags to output a total red blood cell content for the physical sample. However, Block S140 can correlate the extracted features with a red blood cell content via any other suitable non-parametric method or technique.

In the foregoing implementation, Block S130 can segment the portion of the image correlated with the physical sample, and Block S140 can match each segment with a template image to estimate the total red blood cell content of the physical sample. For example, Block S130 can segment the image statically according to predefined segment size and/or shape, such as a square ten-pixel by ten-pixel area. Alternatively, Block S130 can segment the image dynamically, such as according to redness, hue, saturation, shade, brightness, chroma, wavelength range, or any other metric or color of light in the image. Block S130 can also decompose each segment of the image (an 'image segment') into separate color components, such as a histogram of color intensity in the red, green, and blue color spaces, as shown in FIG. 6B. For at least the red color component, Block S140 can then calculate the absolute difference in pixel intensities for pixels in the image segments and pixels in the template images to match each image segment with a suitable template image. Each template image can be contained within a the library of template images, and each template image can be an image of a master sample of known hemoglobin or red blood cell mass, volume, or density. Generally, each template image can include a red blood cell content indicator that, when matched with the image segment, can be converted into a red blood cell blood content for a portion of the physical sample correlated with the image segment. For example, Block S140 can correlate the image segment with a physical dimension of the physical sample by implementing a gauging technique and then determine the type of physical sample to be a surgical sponge gauze or surgical towel by implementing an object recognition technique. In this example, Block S140 can then identify an absorbency of the sample according to a database of absorbency values for different types of samples. Block S140 can finally pass the red blood cell content indicator of the matched template image, the absorbency of the physical sample, and the physical area of the portion of the sample through an algorithm to estimate the red blood cell content of the portion of the physical sample. Block S140 can finally estimate the total red blood cell content of the physical sample by summing each red blood cell content estimate of all segments of the image correlated with the physical sample. Alternatively, the estimated red blood cell content indicators for all of the image segments can be summed and then manipulated according to an overall dimension and/or absorbency of the physical sample to estimate total red blood cell content in the physical sample.

In another implementation, Block S130 extracts features from pixel clusters from a portion of the image, and Block S140 implements a parametric model or function to tag each pixel cluster with a red blood cell content. As described in U.S. patent application Ser. No. 13/544,646, Block S140 can insert one or more extracted features from one pixel cluster into a parametric function to substantially directly transform the extracted feature(s) from the pixel cluster into a red blood cell content. Block S140 can then repeat this for each other pixel cluster in the area of the image correlated with the physical sample. For example, the extracted feature(s) can include any one or more of a color intensity in the red component space, a color intensity in the blue component space, and/or a color intensity in the green component space. In these examples, the parametric function can be a mathematical operation or algorithm that relates color intensity to hemoglobin mass per unit area of the related region of the physical sample. As described in U.S. patent application Ser. No. 13/544,646, reflectance of oxygenated hemoglobin ($HbO_2$) at certain wavelengths of light can be indicative of the concentration of hemoglobin. Furthermore, because the hemoglobin content of a wet (hydrated) red blood cell is typically about 35%, red blood cell content can be extrapolated from the hemoglobin concentration based on a static estimated hemoglobin content (e.g., 35%). Therefore, in another example, Block S130 can extract a reflectance value at a particular wavelength of light for each pixel cluster in a set of pixel clusters in the image, and Block S140 can convert each reflectance value into a hemoglobin concentration value by implementing a parametric model. Block S140 can then combine the hemoglobin concentration values to estimate the total red blood cell content of the physical sample. Additionally or alternatively, Block S140 can implement a lookup table, a regression model, a non-negative least-squares algorithm, or any other suitable algorithm, method, or parametric model to transform one or more extracted features into a red blood cell content estimate for the physical sample.

However, Block S140 can implement any other parametric and/or non-parametric analysis of single pixels or pixel clusters within the image to estimate the red blood cell content of the physical image. Block S240 can implement the same or similar techniques to estimate the red blood cell content of the second physical sample. A time-based history of extracorporeal red blood cells can also be augmented with the output of Block S140 to maintain a current estimate of total patient red blood cell loss.

As shown in FIG. 3, Block S150 of first method S100 recites estimating an extracorporeal blood content of the physical sample based on the estimated red blood cell content of the physical sample. Generally, Block S150 functions to transform the estimated red blood content of the physical sample into a volume of blood components in the physical sample according to a measured hematocrit, an estimated static hematocrit, or an estimated dynamic hematocrit of the patient. In one implementation, Block S150 transforms the estimated red blood cell content into a total blood volume in the physical sample, including red blood cells, plasma, leukocytes, platelets, and plasma. For example, Block S150 can implement the equation

VB=RBC÷HCT.

In another implementation, Block S150 estimates a plasma volume of the physical sample based on the estimated red blood cell content of physical sample. For example, Block S150 can solve for PV in the equation $$HCT = \frac{RBC}{VB} = \frac{RBC}{RBC + PV}.$$

However, Block S150 can estimate the volume of any one or more blood components based on at least the red blood cell content estimate of the physical sample and/or according to any other formula or algorithm.

In one implementation, Block S150 implements a static hematocrit value to convert the red blood cell content to a blood or plasma volume. For example, the static hematocrit value can be a previous hematocrit value that was measured directly (i.e., with a centrifuge that separate components of a sample of the patient's blood), such as at the beginning of a surgery. In another example, the static hematocrit value can be a hematocrit value estimated based on a characteristic and/or demographic of the patient. In this example, Block S150 can interface with Block S180 described below to access a lookup table or algorithm relating patient age, gender, weight, and/or height to an average or predicted hematocrit value. The lookup table or algorithm can also account for a health condition of the patient that may affect the patient's hematocrit, such as anemia, leukemia, myeloma, or an eosinophilic disorder. The static hematocrit value can also be entered by a user, such as an anesthesiologist or a surgeon such as at the beginning or any other time during a surgery, delivery, etc.

In another implementation, Block S150 implements a dynamic hematocrit value to convert the red blood cell content to a blood or plasma volume. As described above, first method S100 can continuously and/or cyclically update the estimated hematocrit of the patient over time, such as in response to each subsequent image of a physical sample or every minute as additional fluid is administered to the patient intravenously. Therefore, in this implementation, Block S150 can access a previous hematocrit estimate (i.e., estimated in a previous application of Block S160) and apply the previous hematocrit estimate to the red blood cell content estimate to generate an estimate of blood volume in the physical sample. For example, Block S150 can select a hematocrit estimate that was generated at approximately the same time that the image of the physical sample was captured. This example may be particularly applicable to the physical sample that is a surgical suction canister. In the implementation in which Block S122 tags the image with a time stamp based on when the physical sample was used, Block S150 can select the hematocrit estimate that was generated at approximately the same time that the physical sample was used. This example may be particularly applicable to the physical sample that is a surgical sponge gauze.

Figure 7:
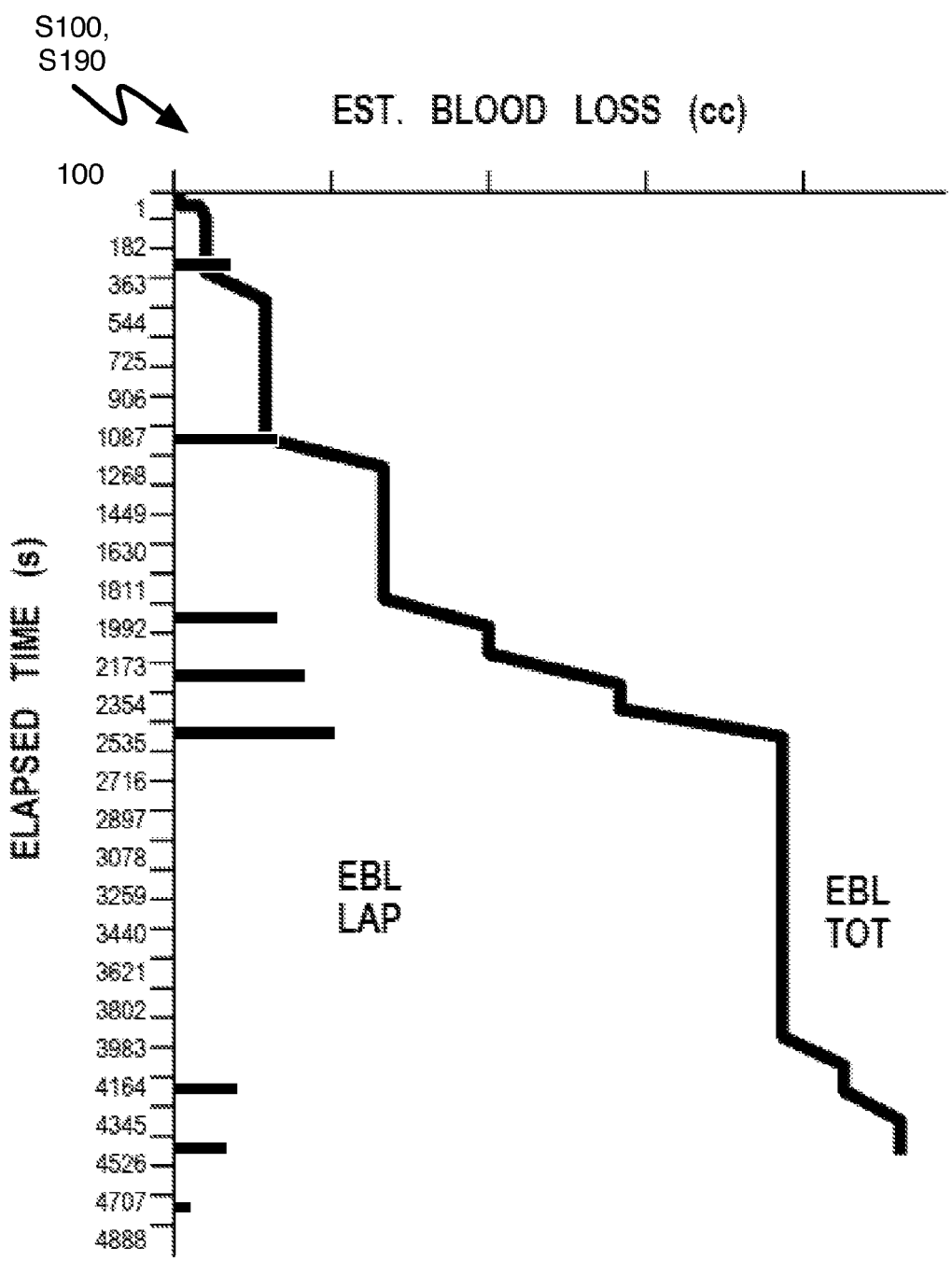
FIG. 7 is a graphical representations in accordance with one variation of the first method.

Block S150 can additionally or alternatively select a most recent hematocrit estimate. However, Block S150 can select the dynamic hematocrit value according to any other schedule or schema. A time-based history of blood loss of the patient can also be augmented with the output of Block S150 to maintain a current estimate of total patient blood loss over time, as shown in FIG. 7.

As shown in FIG. 5, one variation of first method S100 further includes Block S170, which recites tracking loss of a non-blood fluid by the patient. Generally, Block S170 functions to implement techniques similar to those of Blocks S130, S140 and/or S150 to estimate the quantity of other fluids contained in or adsorbed by the physical sample. For example, Block S170 can implement machine vision techniques to identify the presence and volume of saline, ascites, bile, irrigant saliva, gastric fluid, mucus, pleural fluid, urine, fecal matter, or any other bodily fluid of a patient, surgical fluid, particulate, or matter in the physical sample. Block S170 can also access a volume of irrigant used in the surgery and, from this quantitative and qualitative data, distinguish between fluid lost by the patient and fluid collected from irrigation. Block S170 can thus estimate a change in intracorporeal water volume of the patient, such as a change in the level of water or water-based fluids in the gastrointestinal system. Block S160 can then apply an algorithm to estimate the volume of water and/or electrolytes into the patient's circulatory system over time, which can further inform the estimated current hematocrit of the patient in Block S160. However, Block S170 can function in any other way to track patient loss of a non-blood fluid, and first method S100 (e.g., Block S160) can implement data tracked in Block S170 in any other suitable way.

As shown in FIG. 5, one variation of first method S100 further includes Block S180, which recites estimating an initial hematocrit of the patient. Generally, Block S180 functions to transform known qualitative and/or quantitative data of the patient into an estimated initial hematocrit of the patient, such as at the start of a surgery, delivery, or other medical event. As described above, Block S180 can implement a lookup table or algorithm relating patient age, gender, weight, and/or height to an average or predicted hematocrit value. For example, the initial patient hematocrit of a forty-year-old male can be estimated at 47% and the initial patient hematocrit of a fifteen-year-old female can be estimated to be 41%. The lookup table or algorithm can also account for an altitude of the patient or a health condition of the patient that may affect the patient's hematocrit, such as anemia, leukemia, myeloma, an eosinophilic disorder, or a fitness level. Alternatively, Block S180 can receive a direct measurement of the hematocrit of the patient, such as by separating red blood cells and plasma in a blood sample from the patient via centrifuge and then measuring the relative volumes of the separated materials. However, Block S180 can function in any other way to estimate or access an initial hematocrit of the patient.

As shown in FIG. 5, one variation of first method S100 further includes Block S182, which recites estimating an initial intravascular blood volume of the patient. Generally, Block S182 functions to transform known qualitative and/or quantitative data of the patient into an estimated initial patient blood volume, such as at the start of a surgery, delivery, or other medical event. For example, Block S182 can implement a lookup table or an algorithm to estimate the initial patient blood volume based on a weight and a height of the patient. However, Block S182 can additionally or alternatively estimate the patient's initial blood volume based on an age, a gender, a health condition, etc. of the patient. However, Block S182 can function in any other way to estimate the initial blood volume of the patient.

As described in U.S. patent application Ser. No. 13/544,646, first method S100 can further access non-image features, such as weight of the physical sample, a direct measurement of a volume of fluid in the physical sample that is a canister, a clinician-estimated canister fluid volume, a fluid volumes and/or qualities of previous physical samples, previous fluid volumes and/or qualities of the physical sample that is a fluid canister, a sample counter, an ambient lighting condition, a type or other identifier of the physical sample, directly-measured properties of fluid in the physical sample, a patient vital sign, a patient medical history, altitude, an identity of a surgeon, a type of surgery or operation in process, or any other suitable non-image feature. For example, as described below and in U.S. patent application Ser. No. 13/544,646, Blocks of first method S100 can implement any of these non-image features to select template images for comparison with pixel clusters in the selected area, to select of a parametric model or function to transform the extracted feature(s) into a red blood cell count estimate, to define alarm triggers for excess fluid loss or hematocrit change, to transform one or more extracted features into a blood quantity indicator, or to transform one or more extracted features into a quantity or quality of another fluid or solid in the physical sample. However, first method S100 can implement any of these non-image features to modify, enable, or inform any other function or Block of first method S100.

As shown in FIG. 3, Block S160 of first method S100 recites estimating the hematocrit of the patient based on a previous hematocrit of the patient, the quantity of the fluid administered to the patient, and the estimated extracorporeal blood content of the physical sample. Additionally or alternatively, Block S160 can recite estimating an intravascular hematocrit of the patient substantially current to a first time based on an initial intravascular hematocrit of the patient, the estimated first red blood cell content of the first physical sample, and a quantity of fluid administered to the patient intravenously up to the first time, as shown in FIG. 4. Furthermore, Block S260 can recite estimating an intravascular hematocrit of the patient substantially current to a second time based on the estimated intravascular hematocrit of the patient substantially current to the first time, the estimated second red blood cell content of the second physical sample, and a quantity of fluid administered to the patient intravenously up to the second time, as also shown in FIG. 4.

Generally, Block S160 functions to combine several variables related to, directly affecting, and/or indirectly affecting a quality and/or quantity of the patient's intravascular blood volume. Such variables can include fluid (e.g., blood plasma, saline) administered to the patient, blood lost by the patient, non-blood fluids lost or excreted by the patient, adsorption of fluid and electrolytes into or out of the circulatory system, etc., any of which can be dependent on time. Block S160 can also combine any one or more of the foregoing variables with constants also related to intravascular blood quantity and/or quality, such as an initial patient hematocrit (e.g., from Block S180), an initial blood volume (e.g., from Block S182), a composition of a colloid or crystalloid administered to the patient (e.g., from Block S110), etc. Block S260 can similarly function to update the hematocrit estimate of the patient at a later time.

Figure 8:
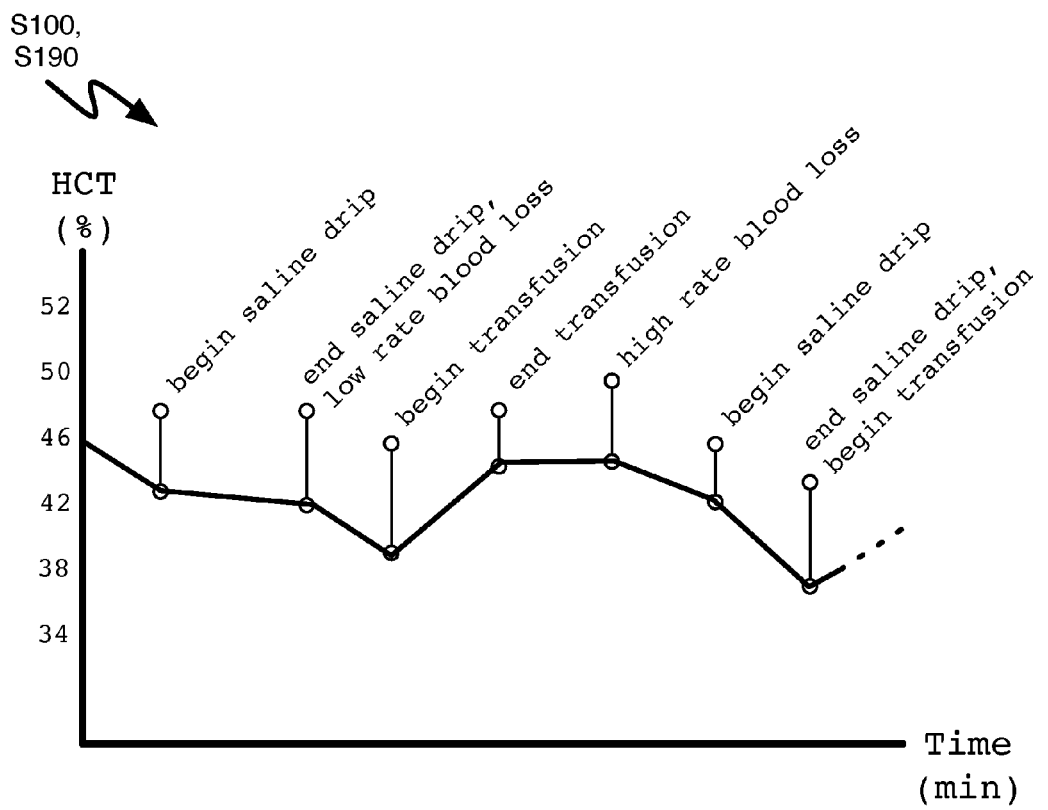
FIG. 8 is a graphical representations in accordance with one variation of the first method.

Block S160 and/or Block S260 can be repeated continuously or cyclically, such as throughout a surgery, delivery, or other medical event, to maintain a substantially current estimate of the hematocrit of the patient, as shown in FIG. 8. For example, Block S160 can repeat (or Block S260 can follow Block S160) in response to retrieval of each subsequent image of each physical sample that is a surgical sponge gauze, surgical towel, etc. and/or in response to retrieval of each subsequent image of a physical sample that is a surgical suction canister, cell salvage canister, etc.

In one implementation, Block S160 (and Block S260) implements a first-order parametric model or algorithm to generate a substantially current estimate of intravascular patient hematocrit based on time-dependent and static variables. For example, hematocrit can be a function of: initial intravascular hematocrit $HCT_o$; initial volume of blood in the patient $VB_o$; red blood cell (or hemoglobin) loss $\Delta RBC_i$; intravenous infusion of saline or other non-blood-based fluid $\Delta S_i$; intravenous transfusion of blood RB and the hematocrit of the transfused blood $HCT_B$; time $(t_i-t_o)$, such as lag in adsorption of saline, previously infused into the patient, out of bloodstream $t_{S,lag}$; etc.

In one example of this implementation, Block S160 can implement the following equations to estimate the intravascular hematocrit of the patient. First, the initial red blood cell count $RBC_o$ at initial time $t_o$ can be estimated based on the initial intravascular hematocrit and blood volume of the patient according to the formulas:

$$HCT_0 = \frac{RBC_0}{VB_0} = \frac{RBC_0}{RBC_0 + PV_0}, \text{ and}$$

$$RBC_o = VB_o \cdot HCT_o.$$

From this, Block S160 can calculate the current intravascular hematocrit of the patient at a subsequent time $t_i$ according to the formula:

$$HCT_i = \frac{(RBC_o - \Delta RBC_i)}{(RBC_o - \Delta RBC_i) + (PV_o + \Delta S_i)},$$

wherein $\Delta RBC_i$ is the change in red blood cell (or hemoglobin) count over time and includes both blood transfusion and (estimated) blood loss from Blocks S140 and S150, and wherein $\Delta S_i$ is intravenous infusion of saline or another non-blood-based fluid of known composition. $\Delta RBC_i$ can be calculated according to the following formula:

$$\Delta RBC_i = -(\Sigma_{n=1}^{i} RBC_{s,n}) + RB \times HCT_B \times (t_i - t_{B,o})$$

wherein $(\Sigma_{n=1}^{i} RBC_{s,n})$ is the sum of estimated red blood cell volumes in all samples, which can be substantially correlated with the total estimated red blood cell loss of the patient. Furthermore, RB is the rate of blood transfusion, $HCT_B$ is the hematocrit of transfused blood, and $RB \cdot HCT_B \cdot (t_i - t_{B,o})$ is the total estimated red blood cell (or hemoglobin) count transfused into the blood steam of the patient between an initial transfusion time $t_{B,o}$ and the current time $t_i$. Finally, $\Delta S_i$ can be calculated according to the formula:

$$\Delta S_i = \begin{cases} RS \cdot (t_i - t_{S,o}) & (t_i - t_{S,o} - r_{S,lag}) \leq 0 \\ RS \cdot (t_i - t_{S,o}) - AS \cdot (RS \cdot (t_i - tS_o)) \cdot (t_i - t_{S,o} - t_{S,lag}) & \text{else} \end{cases}$$

wherein RS is the volume flow rate of saline or other non-blood-based fluid administered to the patient intravenously, AS is an estimated absorbency rate of saline (or water) out of the bloodstream of the patient, and $t_{S,lag}$ is a lag in absorption of saline (or water) out of bloodstream. Block S260 can similarly estimate a subsequent hematocrit of the patient, such as at a later time t'. However, Block S160 and/or Block S260 can estimate the intravascular hematocrit of the patient according to any other model or algorithm.

In other implementations, Block S160 and Block S260 implement a second-, third-, fourth-, or other-order algorithm. Block S160 and Block S260 can also account for any other static or time-dependent variable related to intravascular and/or extracorporeal blood quantity and/or quality.

As shown in FIG. 5, one variation of first method S100 further includes Block S190, which recites tracking the hematocrit of the patient over time according to the previous hematocrit of the patient, the estimated hematocrit of the patient based on the estimated extracorporeal blood content of the physical sample, and subsequent estimated hematocrits of the patient based on estimated extracorporeal blood contents of subsequent physical samples. Generally, Block S190 functions to assemble past and current estimated hematocrit values of the patient into a time-dependent trendline of the patient's intravascular hematocrit. Block S190 can additionally or alternatively output a trend in total blood loss and/or red blood cell loss of the patient over time. From any one or more of these trends, Block S190 can predict a future rate of blood loss, red blood cell loss, and/or change in hematocrit of the patient (shown in FIG. 8) and thus predict a future blood-related need of the patient. For example, Block S190 can analyze trend data to predict a future time at which the intravascular hematocrit of the patient will drop below a threshold safety level (e.g., 34%). In light of this prediction, a surgeon, nurse, anesthesiologist, doctor, or other user can replace a saline drip line with a blood transfusion line substantially before the safety of the patient is threatened (i.e., before the hematocrit of the patient drops below the threshold safety level). Block S190 can therefore analyze estimated blood quality and/or quantity data output in any one or more of the foregoing Blocks of first method S100 to predict a future need of the patient and thus enable a doctor or other medical staff to make preemptive medical decisions, thereby potentially reducing patient risk. However, Block S190 can function in any other way to track the hematocrit of the patient over time and/or predict a future blood-related need of the patient.

As shown in FIG. 5, one variation of first method S100 includes Block S192, which recites triggering an alarm in response to the estimated hematocrit of the patient falling outside a predefined range of suitable hematocrit values. Generally, Block S192 functions to interface with Block S160, S260, and/or Block S190 to inform a user (e.g., medical staff) of an estimated current or predicted future blood-related value that falls outside of a suitable range of values. Block S192 can provide an alarm (i.e., warning) provided through any of an audible alarm, a visual alarm, a digital display, etc. The alarm can be any of a warning that the patient's hematocrit is currently too low, a warning that the patient's hematocrit is approaching a threshold level, a warning that the patient has lost a threshold volume of blood or red blood cells, a warning that the patient is approaching a blood volume or blood volume percentage loss outside of an acceptable range, a warning that current infusion or transfusion fluids may be improper for patient care past a certain time or infused volume, a warning of patient risk level, such as for hypovolemic or hypervolemic shock, an estimated patient hemorrhage classification, or any other suitable warning.

Block S192 can additionally or alternatively provide suggestions related to patient care, such as to start or stop intravenous transfusion or infusion, to set a particular volume or volume flow rate of transfused or infused fluid, to respond to a hemorrhage, to delay a surgical operation until a patient condition reaches an acceptable status, to speed up a surgical operation before a patient condition reaches a certain status, or any other suitable suggestion. The warning and/or suggestion can also account for the age, weight, gender, health, or other demographic of the patient. Block S192 can further access an electrocardiogram (EKG) machine, an oximeter (e.g., a finger-type blood oxygen monitor), an IV drip monitor, or other monitor or sensor connected to the patient, or a medical record of the patient to further inform the warning or suggestion. For example, an oximeter connected to the patient that shows a substantially low oxygen level in the blood of the patient can verify a substantially low estimate of patient intravascular hematocrit. In another example, Block S192 accesses a medical record of the patient that indicates that the patient has chronic kidney disease, which necessitates a minimum viable intravascular hematocrit level greater than that of a similar patient without chronic kidney disease. However, Block S192 can function in any other way, access any other data, and provide any other warning or suggestion.

2. Second Method

Figure 11:
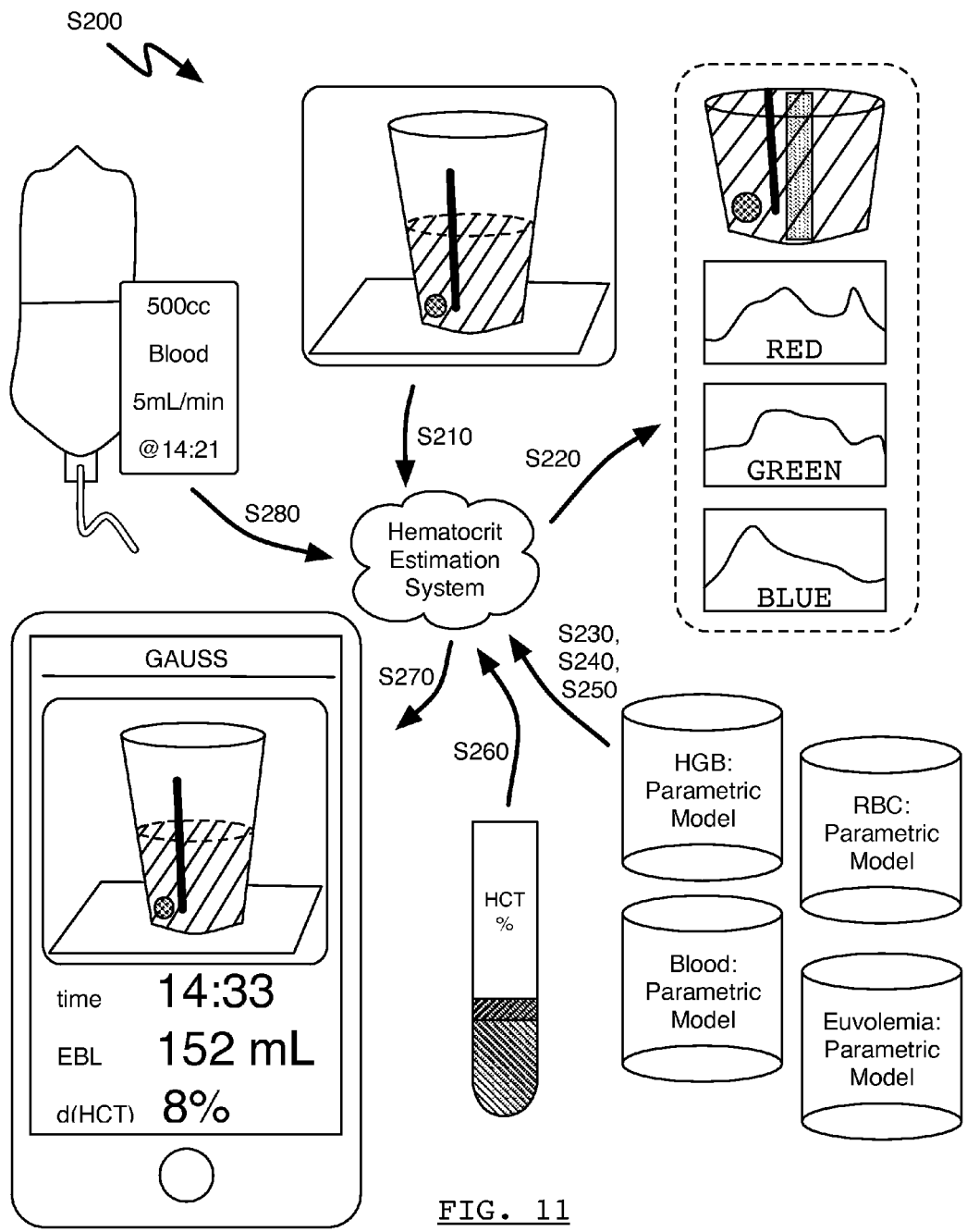
FIG. 11 is a flowchart representation of a second method.

As shown in FIG. 11, method S200 for managing blood loss of a patient, includes: receiving an image of a physical sample in Block S210; extracting a feature from an area of the image corresponding to the physical sample in Block S220; estimating a blood volume indicator of the physical sample according to the extracted feature in Block S230; estimating a patient blood loss based on the blood volume indicator in Block S240; estimating a euvolemic patient hematocrit based on an estimated patient blood volume and the estimated patient blood loss in Block S250; receiving a measured patient hematocrit in Block S260; and generating a volemic status indicator based on a comparison between the measured patient hematocrit and the estimated euvolemic patient hematocrit in Block S270.

Generally, second method S200 implements techniques described above to estimate a volume of patient blood loss over time through image processing of physical samples containing blood and to output a volemic status indicator that defines a metric of patient intracirculatory blood status. Second method S200 calculates the volemic status indicator based on a comparison between a measured patient hematocrit and an estimated euvolemic patient hematocrit (i.e., a quantitative difference between these values). The estimated euvolemic patient hematocrit can be based on a previous (measured or estimated) patient hematocrit, an estimated (initial or recent) patient blood volume, and an estimated patient blood loss, wherein the euvolemic patient hematocrit defines an estimated intracirculatory hematocrit of the patient if the estimated volume of patient blood loss is replaced perfectly with saline. The measured patient hematocrit can be a tested (e.g., actual) patient hematocrit value, such as measured with a non-invasive optical intracirculatory hematocrit monitor outputting measured hematocrit values on a regular time interval or measured by centrifuging a sample of the patient's blood. Patient hematocrit can also be stated in terms of the patient hemoglobin concentration (e.g., HGB (g/dL)), which is experimentally correlated with patient hematocrit according to a mean corpuscular volume (MCV) of the patient's erythrocytes. Second method S200 therefore generates the volemic status indicator that defines a magnitude of patient deviation from euvolemia. The volemic status indicator can define a composite of the effectiveness of intravenous fluid replenishment and insensible intracirculatory fluid losses (e.g., internal bleeding, sweating, evaporation from open incisions) of the patient.

Similar to first method S100 described above, second method S200 can therefore be useful to a surgeon, an anesthesiologist, a nurse, etc. in an operating room and/or during a surgery to manage fluid replacement and/or blood component therapy.

Figure 12:
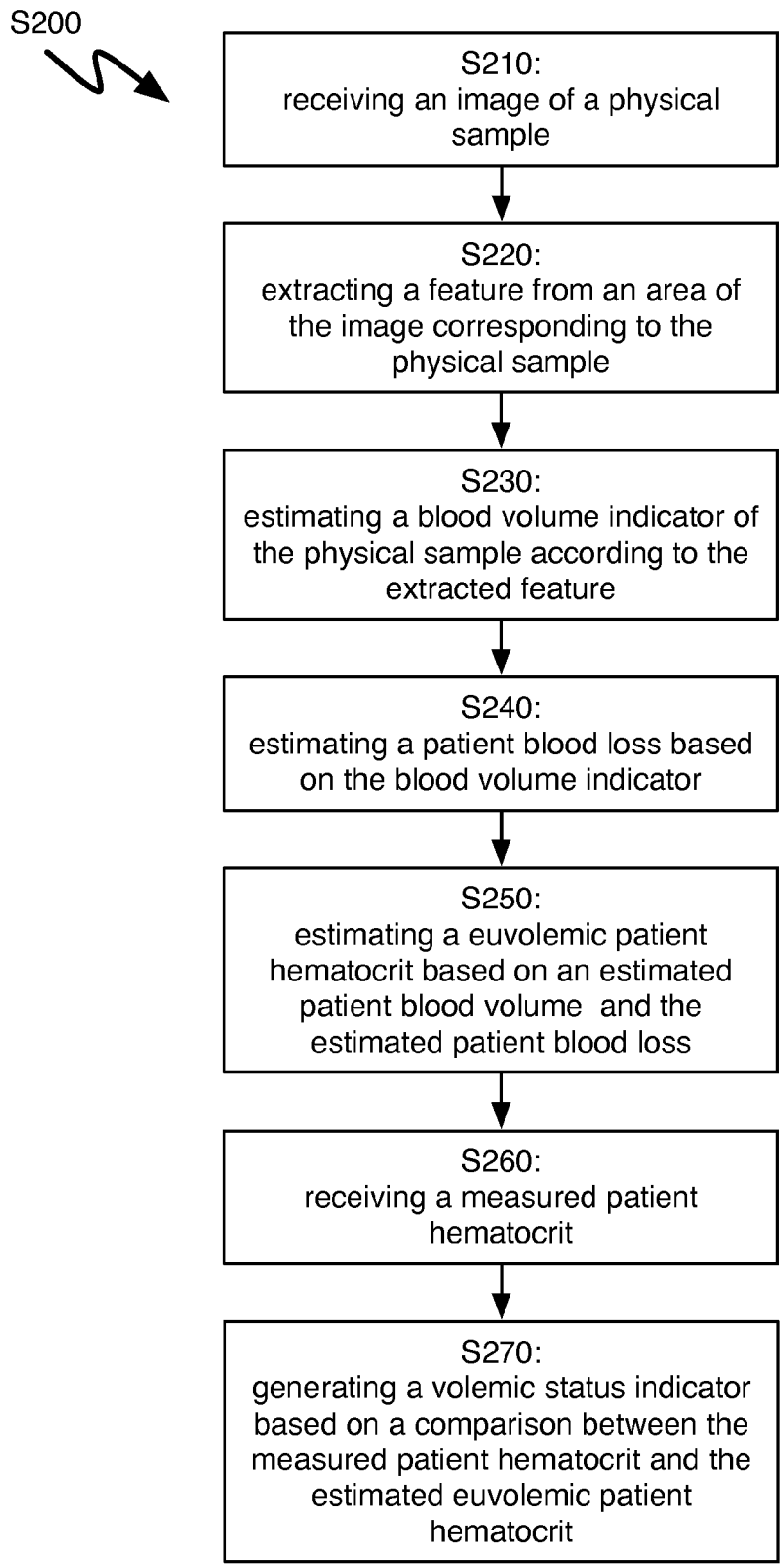
FIG. 12 is a flowchart representation of one variation of the second method.

As shown in FIGS. 11 and 12, Block S210 of second method S200 recites receiving an image of a physical sample. Generally, Block S210 can implement techniques similar to Block S120 described above. For example, Block S210 can receive a static color image of the physical sample from an optical sensor, wherein the physical sample is one of a surgical gauze sponge, a surgical towel, a surgical dressing, a surgical suction canister, and a cell salvage canister. However, Block S210 can function in any other way to receive an image of the physical sample.

As shown in FIGS. 11 and 12, Block S220 of second method S200 recites extracting a feature from an area of the image corresponding to the physical sample. Generally, Block S220 can implement techniques similar to Block S130 described above. For example, Block S220 can extract a color intensity value of a set of pixels within the area of the image. However, Block S220 can function in any other way to extract any other feature from any area of the image.

As shown in FIGS. 11 and 12, Block S230 of second method S200 recites estimating a blood volume indicator of the physical sample according to the extracted feature. Generally, Block S230 can implement techniques similar to Block S140 and Block S150 described above. Block S230 can estimate the blood volume indicator that includes a volume or other quantitative measure of the hemoglobin content of the physical sample, a volume or other quantitative measure of the red blood cell content of the physical sample, a volume or other quantitative measure of blood the physical sample, a volume or other quantitative measure of the plasma content of the physical sample, a volume or other quantitative measure of the white blood cell content of the physical sample, or any other a volume or other quantitative measure of blood or a blood component within the physical sample. For example, as described above, Block S230 can implementing a parametric model to transform a color intensity value (extracted in Block S220) into a quantity of red blood cells in the physical sample. However, Block S230 can function in any other way to estimate any type or form of blood volume indicator in the physical sample in any other suitable way.

As shown in FIGS. 11 and 12, Block S240 of second method S200 recites estimating a patient blood loss based on the blood volume indicator. Generally, Block S240 can implement techniques similar to Block S150 described above. In one implementation described above, Block S230 estimates a mass of hemoglobin, in a surgical gauze sponge, and Block S240 estimates the volume of blood in the surgical gauze sponge by converting the estimated hemoglobin mass to a red blood cell volume, and converting the estimated red blood cell volume to blood volume according to a known or estimated hematocrit of the patient. In this implementation, Block S240 can apply a static estimated hematocrit, a most-recently estimated patient hematocrit, an estimated hematocrit around an estimated use time of the surgical sponge (e.g., based on an image time stamp), or a recently measured hematocrit value (e.g., measured with a non-invasive optical intracirculatory hematocrit monitor) to convert the estimated red blood volume to an estimated extracorporeal blood volume. In another implementation, Block S230 estimates the volume of red blood cells in a surgical suction canister, and Block S240 estimates the volume of blood in the suction canister over time by applying a time-dependent hematocrit value to each subsequent image of the suction canister as the suction canister fills over time.

Figure 14:
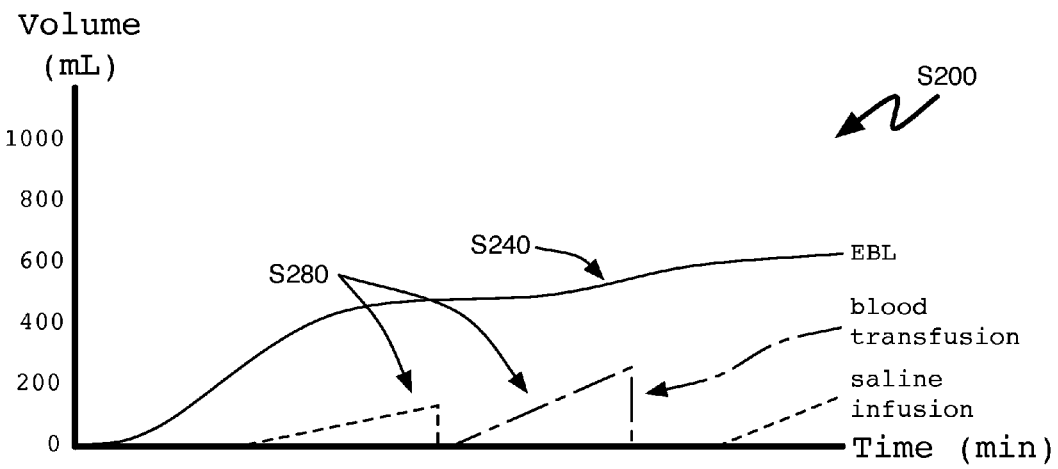
FIG. 14 is a graphical representation of one variation of the second method.

Block S240 can also update a total estimated blood loss volume of the patient with the estimated blood volume in the physical sample. For example, Block S240 can maintain a running total of patient blood loss by adding the estimated volume of blood in each subsequent physical sample to a previous total. As shown in FIG. 14, Block S240 can also output a time-dependent chart (e.g., graph) of total patient blood loss including the estimated patient blood loss and an aggregate of estimated blood volumes of a set of previous physical samples. However, Block S240 can function in any other way to estimate a patient blood loss based on the blood volume indicator of the physical sample.

As shown in FIGS. 11 and 12, Block S250 of second method S200 recites estimating a euvolemic patient hematocrit based on an estimated patient blood volume and the estimated patient blood loss. Generally, Block S250 functions to estimate a euvolemic hematocrit of the patient by estimating the hematocrit of the patient if the total estimated volume of patient blood loss were replaced with saline. Block S250 therefore outputs a hypothetical value of patient hematocrit that assumes constant intracirculatory blood volume (i.e., euvolemia) in which patient euvolemia is maintained through infusion of crystalloid (i.e. saline). In particular, as blood, including red blood cells, is lost and the blood volume loss is replenished with crystalloid, the patient's intracirculatory blood is diluted, and Block S250 outputs a measure of this hypothetical hemodilution in the form of an estimated euvolemic patient hematocrit. In one example, Block S250 functions to estimate a euvolemic hematocrit of the patient by estimating the hematocrit of the patient according to a euvolemic blood model specifying intracirculatory replenishment of a total estimated volume of patient blood loss with saline.

In one implementation, Block S250 subtracts the estimated blood volume in the physical sample from a previous estimated total intracirculatory blood volume of the patient to calculate a new total intracirculatory blood volume, converts the new total intracirculatory blood volume into an intracirculatory red blood cell volume (or mass) according to a previous patient hematocrit, and divides the intracirculatory red blood cell volume by the sum of the original total intracirculatory blood volume (i.e., the sum new total intracirculatory blood volume and the volume of saline replenishment) to estimate the euvolemic patient hematocrit. Alternatively, because hemoglobin mass and red blood cell volume are correlated, Block S250 can similarly convert the new total intracirculatory blood volume into an intracirculatory hemoglobin mass according to a previous patient hematocrit and divide the intracirculatory hemoglobin mass by the sum of the original total intracirculatory blood volume to estimate the euvolemic patient hematocrit. In this alternatively, Block S250 can output euvolemic patient hematocrit in the form of hemoglobin mass per (deci-) liter of blood (i.e., HGB g/dL).

Therefore, Block S250 can further receive a measured patient hematocrit from an optical intracirculatory hematocrit monitor coupled to the patient (e.g., arranged on a patient's finger). Block S250 can alternatively receive the measured patient hematocrit from an electronic medical record (e.g., laboratory-run hematocrit), or from a bedside spot-check device (e.g. an intraoperative assay of hematocrit), and Block S250 can receive the measured patient hematocrit continuously, or semi-continuously, on a constant or varying interval, or according to any other schedule.

Alternatively, Block S250 can implement a previously-estimated patient hematocrit or estimate an initial patient hematocrit according to a weight of the patient, a height of the patient, a gender of the patient, an age of the patient, and/or a health status of the patient, etc. Block S250 can similarly estimate the total patient intracirculatory blood volume according to the weight of the patient, the height of the patient, the gender of the patient, the age of the patient, and/or the health status of the patient, etc. Block S250 can alternatively receive an estimated total patient intracirculatory blood volume, such as from an anesthesiologist through a touch display following a user tracer-based intracirculatory blood volume test, or implement an intracirculatory patient hematocrit from a previous timestep. However, Block S250 can function in any other way to estimate a euvolemic patient hematocrit.

Figure 15:
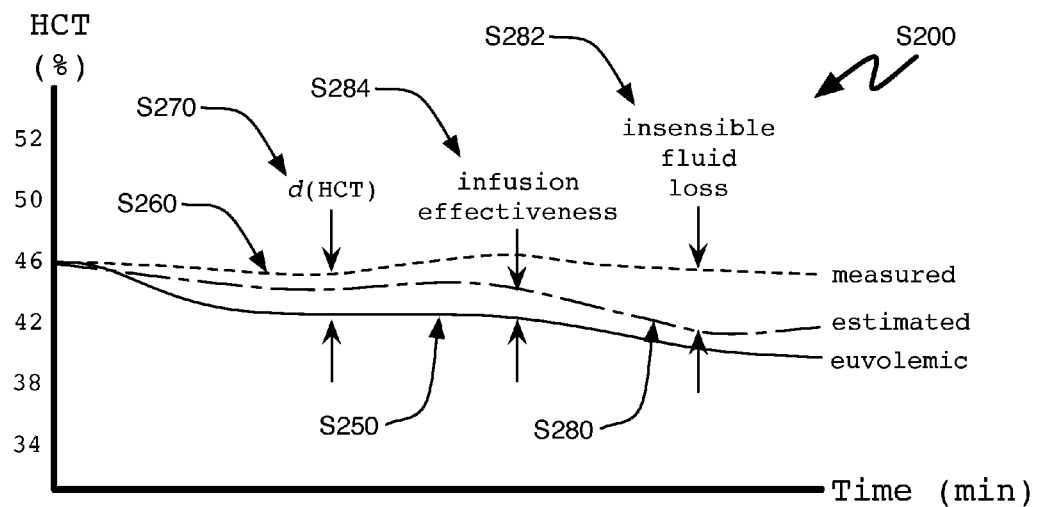
FIG. 15 is a graphical representation of one variation of the second method.

As shown in FIGS. 11, 12, and 15, Block S260 of second method S200 recites receiving a measured patient hematocrit. Generally, Block S260 functions to collect a real (i.e., measured, actual) hematocrit of the patient such that Block S270 can compare the estimated euvolemic hematocrit to a real hematocrit of the patient. For example, Block S260 can interface with an optical intracirculatory hematocrit monitor to receive measured patient hematocrits from the optical intracirculatory hematocrit monitor on a regular time interval, such as every thirty seconds. Alternatively, Block S260 can receive manual measured hematocrit entries, such as entered by a nurse through a user interface displayed on a touchscreen arranged within an operating room. However, Block S260 can function in any other way to receive a measured hematocrit of the patient.

As shown in FIGS. 11 and 12, Block S270 of second method S200 recites generating a volemic status indicator based on a comparison between the measured patient hematocrit and the estimated euvolemic patient hematocrit. Generally, Block S270 subtracts the estimated euvolemic hematocrit from the measured hematocrit of the patient to calculate the volemic status indicator (i.e., a magnitude of divergence from euvolemia). As described above, the magnitude of divergence from euvolemia can indicate an effectiveness of intravenous fluid replenishment and quantify insensible intracirculatory fluid losses, such as from internal bleeding, sweating, or evaporation from an open incision.

As shown in FIG. 15, Block S270 can also output a time-dependent chart including the volemic status indicator and a set of previous volemic status indicators. Block S270 can display this chart to a user, such as through a touchscreen arranged within an operating room, to enable the user to monitor blood quality, fluid infusion effectiveness, and other blood related events over time. For example, an anesthesiologist can identity internal bleeding based on an increasing magnitude of divergence from euvolemia over time despite saline or blood infusion. However, Block S270 can function in any other way to output a volemic status indicator of any other form.

Figure 13:
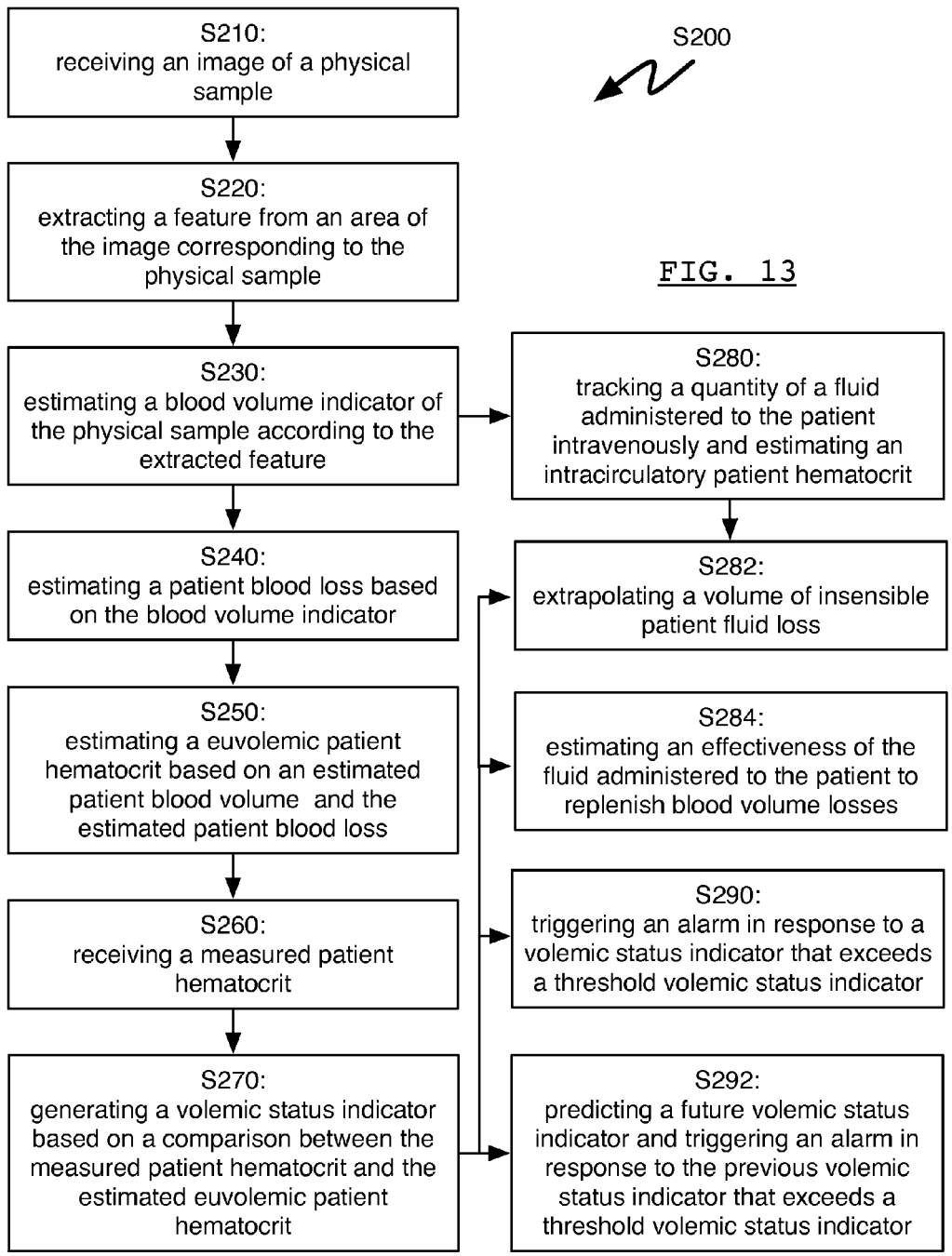
FIG. 13 is a flowchart representation of one variation of the second method.

As shown in FIGS. 13 and 14, one variation of second method S200 includes Block S280, which recites tracking a quantity of a fluid administered to the patient intravenously and estimating an intracirculatory patient hematocrit based on a previous patient hematocrit, the estimated patient blood loss, a quantity of a fluid administered to the patient, and the estimated patient blood volume. Generally, Block S280 implements techniques similar to first method S100 described above. In one implementation, Block S280 tracks intravenous administration of allogeneic blood from a blood transfusion bag to the patient and estimates the intracirculatory patient hematocrit based on the hematocrit of allogeneic blood in the transfusion bag. In this implementation, Block S280 can further receive a second image of the blood transfusion bag, extract a color-related feature from an area of the second image corresponding to the blood transfusion bag, and estimate the hematocrit of allogeneic blood in the blood transfusion bag based on the color-related feature. As described above, Block S280 can also track administration of a crystalloid fluid, of a known composition, to the patient and can estimate the hematocrit of the patient further based on the known composition of the crystalloid fluid.

As shown in FIG. 15, Block S280 can further plot the estimated intracirculatory patient hematocrit with a set of previous estimated intracirculatory patient hematocrits in a first time-dependent chart. Block S280 can additionally or alternatively plot the volume of fluid administered to the patient in a second time-dependent chart. However, Block S280 can function in any other way to track a quantity of a fluid administered to the patient and to estimate an intracirculatory patient hematocrit, and Block S280 ca output any other this blood-related data in any other suitable format.

As shown in FIGS. 13 and 15, one variation of second method S200 includes Block S282, which recites extrapolating a volume of insensible patient fluid loss from a difference between the estimated intracirculatory patient hematocrit and the measured patient hematocrit. Generally, Block S282 functions to subtract the estimated intracirculatory patient hematocrit from the measured patient hematocrit, which can provide a quantitative measure of divergence from an expected patient hematocrit. In particular, Blocks of second method S200 track volumes of saline infusion, blood transfusion, blood loss, and/or other quantitative exchanges of fluids of known or estimated qualities, and Block S280 estimates an intracirculatory patient hematocrit based on these known factors. Block S282 subsequently compares the measured and estimated intracirculatory patient hematocrits, which can provide insight into an intracirculatory blood status of the patient. For example, a large divergence between the measured and estimated intracirculatory patient hematocrits can indicate that the patient is bleeding internally, and Block S290 can trigger an alarm in response to such divergence that exceeds a threshold divergence. Divergence between the measured and estimated intracirculatory patient hematocrits can also indicate a rate of evaporation from an open incision, a rate of absorption of fluid out of the bloodstream (which can indicate a hydration level), internal bleeding, pooling, etc.

Generally, Block S282 can extrapolate a measure of regulation and/or loss of fluid out of the patient's intravascular space, including a comparison of total blood volume and peripheral venous blood volume, and a measured hematocrit received in Block S260 (i.e., a peripheral venous hematocrit) can indicate red blood cell concentration in the patient's vascular system. As part of a body's natural fluid regulation, a patient's body may experience hemoconcentration and/or hemodilution between the vascular system and interstitial spaces. For example, during heaving lifting or a work out, a muscle may "pump" as the body sends blood into peripheral spaces to aid a muscle recovery, which engorges the muscle, and hematocrit in the region of the muscle may therefore shift due to internal fluid replacement. Similarly, during acute hemorrhage, a body may replace fluid internally and local to the hemorrhage, and Block S250 can output the volemic status indicator that incorporates a body's fluid dynamics into one metric that is deviation from euvolemia. By comparing the estimated intracirculatory patient hematocrit and the measured patient hematocrit, Block S282 can thus output a quantitative measure of a patient's body dynamics.

As shown in FIGS. 13 and 15, one variation of second method S200 includes Block S284, which recites estimating an effectiveness of the fluid administered to the patient to replenish blood volume losses based on a difference between the estimated intracirculatory patient hematocrit and the estimated euvolemic patient hematocrit. Generally, Block S282 subtracts the estimated intracirculatory patient hematocrit from the estimated euvolemic patient hematocrit to output a quantitative value of the effectiveness of a fluid infusion (e.g., saline) to maintain patient euvolemia.

As shown in FIG. 13, one variation of second method S200 includes Block S290, which recites triggering an alarm in response to a volemic status indicator that exceeds a threshold volemic status indicator. Generally, Block S290 can trigger an alarm if the volemic status indicator that exceeds a threshold volemic status indicator, which can indicate that the quality of intracirculatory blood of the patient has exceeded an acceptable volume or quality change. As described above, Block S290 can similarly trigger an alarm in response to divergence between measured and estimated intracirculatory patient hematocrits that exceeds a threshold divergence. Block S290 can trigger an audible, visual, or other suitable alarm. Block S290 can also trigger administration of a saline infusion, a blood transfusion, a plasma infusion, etc. However, Block S290 can respond to a volemic status indicator (or other blood status indicator) in any other suitable way.

As shown in FIG. 13, one variation of second method S200 includes Block S292, which recites predicting a future volemic status indicator according a difference between the volemic status indicator and a previous volemic status indicator and triggering an alarm in response to the previous volemic status indicator that exceeds a threshold volemic status indicator. Generally, Block S292 functions to extrapolate a future volemic status based on two or more previous volemic status indicators. Similar to Block S290, Block S292 can compare the predicted volemic status indicator with a volemic status indicator threshold and trigger an alarm or respond in any other suitable way in response to the predicted volemic status indicator that exceeds the volemic status indicator threshold. However, Block S292 can function in any other way to predicting a future volemic status indicator 3. System As shown in FIG. 9, a system 100 for managing blood loss of a patient includes: an interface 102 that receives data related to intravenous administration of a fluid to the patient; an optical sensor 110; a processor 120 coupled to the optical sensor 110 and to the interface 102; a software module 122 executing on the processor 120 and instructing the optical sensor 110 to capture an image of a physical sample, the software module 122 further instructing the processor 120 to track a quantity of the fluid administered to the patient according to data received by the interface 102, to estimate a red blood cell content of the physical sample based on a feature extracted from the image, and to estimate a hematocrit of the patient based on a previous hematocrit of the patient, the fluid administered to the patient, and the estimated red blood cell content of the physical sample; and a display 130 coupled to the processor 120 and receiving instruction from the software module 122 to display the estimated hematocrit of the patient.

The system 100 functions to implement first method S100 described above, wherein the optical sensor (e.g., camera) implements Block S122 to capture the image of the canister and the processor 120 implements Blocks S110, S120, S130, S140, S150, S160, S220, S240, S260, etc. described above according to the software module 122 to continuously and/or cyclically estimate a current intravascular hematocrit of the patient. A surgeon, nurse, anesthesiologist, gynecologist, doctor, soldier, or other user can implement the system 100 to track the intravascular hematocrit of the patient over time, such as during a surgery, childbirth, or other medical event. The system 100 can also detect presence of blood in the physical sample(s), compute patient blood loss rate, estimate patient risk level (e.g., hypovolemic shock), determine hemorrhage classification of a patient. However, the system 100 can perform any other suitable function.

Figure 9:
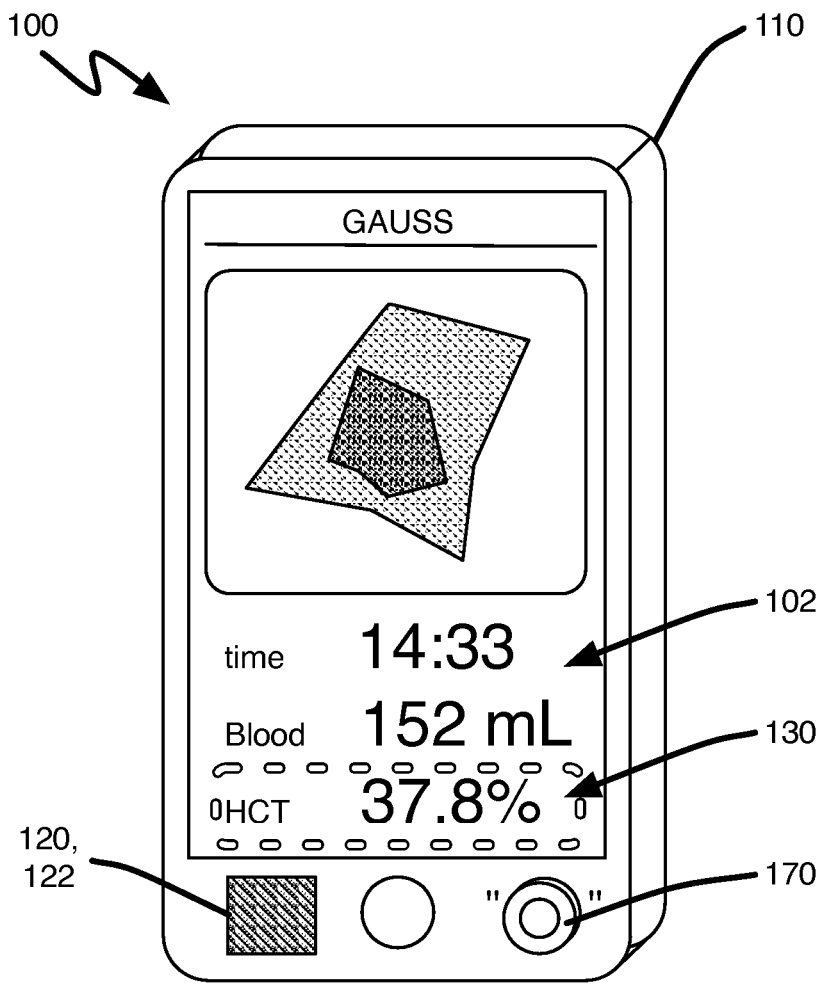
FIG. 9 is a schematic representation of a system of one embodiment.
Figure 10:
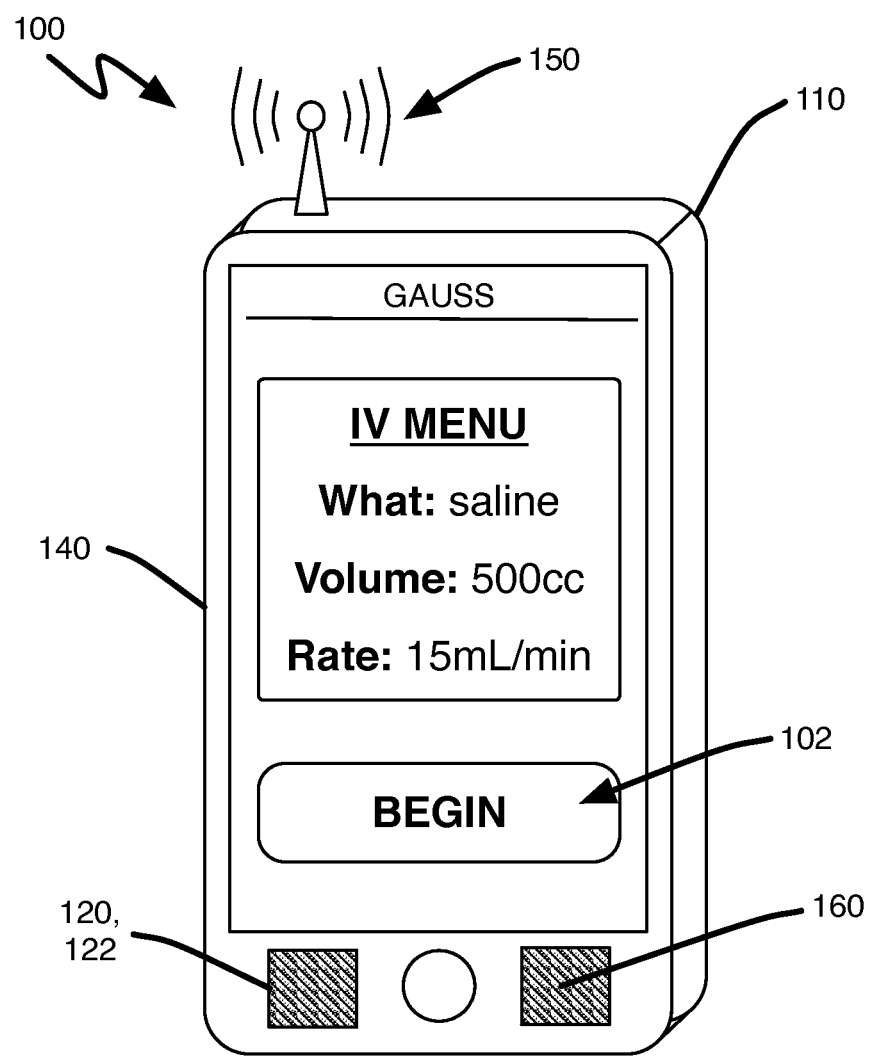
FIG. 10 is a schematic representation of a variation of the system.

As shown in FIGS. 9 and 10, the system 100 can be a handheld (e.g., mobile) electronic device, such as a smartphone or tablet running an image-based blood estimation application (or app) and including the optical sensor 110, the processor 120, and the display 130. Alternatively, the components of the system 100 can be substantially discreet and distinct (i.e., not contained within a single housing). For example, the optical sensor 110 can be a camera arranged substantially permanently within an operating room, wherein the camera communicates with a local network or a remote server (including the processor 120) on which the image of the canister is analyzed (e.g., according to first method S100), and wherein a display 130 that is a computer monitor, a television, or a handheld (mobile) electronic device accesses and displays the output of the processor 120. The interface 102 can further be embodied as touch sensor component of the display 130 of the electronic device that includes a touchscreen. However, the system 100 can be of any other form and/or include any other component.

The system 100 can be used in a variety of settings, including in a hospital setting, such as in a surgical operating room, in a clinical setting, such as in a delivery room, in a military setting, such as on a battlefield, or in a residential setting, such as to aid a consumer in monitoring blood quality and quantity during menorrhagia (heavy menstrual bleeding) or epistaxis (nosebleeds). However, the system 100 can be applicable to any other setting.

The interface 102 of the system 100 functions to receive data related to intravenous administration of a fluid to the patient. Generally, the interface 102 defines an input region through which a user can enter infusion and/or transfusion details. For example, a nurse, surgeon, or anesthesiologist can enter, through the interface 102, the type, total volume, flow rate, and start time of a crystalloid or colloid fluid administered to the patient intravenously, as shown in FIG. 10.

The interface 102 can be any suitable type of interface. In one example, the interface 102 is a keyboard connected to a local computer (e.g., desktop or laptop computer) containing the processor 120, the optical sensor no, and the display 130. Alternatively, the interface 102 can be a sensor component of a touchscreen integrated into a mobile electronic device (e.g., a smartphone, a tablet), wherein the electronic device includes the optical sensor 110 and the processor 120, and wherein the output portion of the touchscreen defines the display 130. The interface 102 can alternatively interface with an IV drip sensor to estimate the flow rate of fluid administered to the patient, and the interface can further receive an image of an IV bag and analyze the image to estimate the volume and/or contents of the IV bag, as described above. However, the interface 102 can function in any other way to receive manual or automatic entry of data pertaining to fluid administered to the patient intravenously. The interface 102 can further receive data pertaining to administration of multiple different fluids simultaneously or in series, such as a simultaneous administration of saline and red blood cells or consecutive administration of saline and then blood.

The optical sensor 110 of the system 100 functions to capture the image of the physical sample. Generally, the optical sensor 110 can implement Block S122 of first method S100 described above, as controlled by the software module 122. In one example implementation, the optical sensor 110 is a digital camera that captures a color image of the physical sample or an RGB camera that captures independent image components in the red, green, and blue component spaces. However, the optical sensor 110 can be any number and/or type of cameras, charge-coupled device (CCD) sensors, complimentary metal-oxide-semiconductor (CMOS) active pixel sensors, or optical sensors of any other type. However, the optical sensor 110 can function in any other way to capture the image of the physical sample, such as in any suitable form or across any suitable visible or invisible spectra.

In one implementation, the optical sensor 110 is a camera arranged within a handheld electronic device. In another implementation, the optical sensor 110 is a camera or other sensor configured to be mounted on a pedestal for placement in an operating room, configured to mount to a ceiling over an operating table, configured for attachment to a battlefield helmet of a field nurse, configured to mount to a standalone hematocrit estimation system including the interface 102, the processor 120, the display 130, and a staging tray that supports the physical sample for imaging, or configured for placement in or attachment to any other object or structure.

According to instructions from the software module 122, the processor 120 of the system 100 tracks a quantity of the fluid administered to the patient according to data received by the interface 102, estimates a red blood cell content of the physical sample based on a feature extracted from the image, and estimates a hematocrit of the patient based on a previous hematocrit of the patient, the fluid administered to the patient, and the estimated red blood cell content of the physical sample. Generally, the processor 120 implements one or more Blocks of first method S100 described above according to instructions from the software module 122. The processor 120 can further repeat execution of these instructions in response to additional images of additional physical samples over time to generate a trendline of estimated patient hematocrit over time. The processor can therefore receive and analyze images of any one or more suitable types (e.g., static, streaming, .MPEG, .JPG, .TIFF) and/or images from one or more distinct cameras or optical sensors.

The processor 120 can be coupled to the optical sensor no, such as via a wired connection (e.g., a trace on a shared PCB) or a wireless connection (e.g., a Wi-Fi or Bluetooth connection), such that the processor 120 can access the image of the physical sample captured by the optical sensor no or visible in the field of view of the optical sensor no. In one implementation, the processor 120 is arranged within a handheld electronic device that also contains the optical sensor 110 and the display 130. In another implementation, the processor 120 is a portion of or is coupled to a remote server, wherein image data from the optical sensor 110 is transmitted (e.g., via an Internet or local network connection) to the processor 120 that is remote, wherein the processor 120 estimates the extracorporeal red blood cell content and/or blood volume in the physical sample and estimates the hematocrit of the patient based on the estimated red blood cell content and/or blood volume, and wherein the hematocrit estimate is transmitted to the display 130.

In one implementation and as described above, the processor 120 can estimate the red blood cell content in the physical sample by matching a portion of the image of the physical sample to a template image, wherein the template image is one template image in a library of template images. For example, the system 100 can further include a data storage module 160 configured to store a library of template images of known contents and/or concentrations of the red blood cells. In this implementation, the processor can correlate the extracted features with the red blood cell count by comparing a feature extracted from the image with a template image in the library of template images, as described above. Alternatively and as described above, the processor 120 can implement a parametric model to estimate the red blood cell content in the physical sample based on the feature extracted from the image.

The processor 120 is further coupled to the interface 102 to receive data pertaining to administration of fluid to the patient over time. For example, the processor 120 can receive, from the interface 102, the type, total volume, flow rate, and start time of administration of a fluid into the patient. From this initial data, the processor 120 can integrate the flow rate over time, in light of the composition of the administered fluid and the total volume of the IV bag, to determine the total volume, parts, mass, weight, etc. of fluid, blood cells, electrolytes, etc. delivered to the patient up to any given time.

The processor 120 further implements Block S160 described above to aggregate multiple variables related to, directly affecting, and/or indirectly affecting a quality and/or quantity of the patient's intravascular blood volume. As described above, such variables can include fluid (e.g., blood plasma, saline) administered to the patient, blood lost by the patient, non-blood fluids lost or excreted by the patient, adsorption of fluid and electrolytes into or out of the circulatory system, etc., any of which can be dependent on time, as well as initial patient hematocrit, an initial blood volume, a composition of a colloid or crystalloid administered to the patient, etc. The processor can therefore continuously and/or cyclically estimate the hematocrit of the patient over time in light of further blood loss (e.g., as determined through analysis of images of additional physical samples) and further intravenous administration of fluids (e.g., based on data collected by the interface 102).

The software module 122 of the system 100 functions to control the interface 102, the optical sensor 110, the processor 120, and the display 130 to receive patient IV data, capture the image of the physical sample, analyze the image, and estimate the hematocrit of the patient. The software module 122 can execute on the processor 120 as an applet, a native application, firmware, software, or any other suitable form of code to control processes of the system 100. Generally, the software module controls implementation of Blocks of first method S100 described above within the system 100, though the software module 122 can control and/or implement any other suitable process or method on or within the system 100.

In one example application, the software module 122 is a native application installed on the system 100 that is a handheld (i.e., mobile) computing device, such as a smartphone or tablet. When selected from a menu within an operating system executing on the computing device, the software module 122 opens, interfaces with a user to initialize a new case, receives IV data through the interface 102 that includes a touchscreen, controls the optical sensor 110 integrated into the computing device to capture the image of the physical sample, implements machine vision and executes mathematical algorithms on the processor 120 to estimate the quantity of red blood cells in the physical sample and the hematocrit of the patient, and controls the display 130 to render the estimated current hematocrit of the patient, as shown in FIG. 9. However, the software module 122 can be of any other form or type and can be implemented in any other way.

The display 130 of the system 100 renders the estimated hematocrit of the patient. The display 130 can be arranged within the handheld electronic device (e.g., smartphone, tablet, personal data assistant) that also contains the optical sensor 110 and the processor 120. The display 130 can also be physically coextensive with the interface, such as in one implementation of the system 100 that is a handheld electronic device including a touchscreen. Alternatively, the display can be a computer monitor, a television screen, or any other suitable display physically coextensive with any other device. The display 130 can be any of an LED, OLED, plasma, dot matrix, segment, e-ink, or retina display, a series of idiot lights corresponding to estimated hematocrit ranges, or any other suitable type of display. The display 130 can further be in communication with the processor 120 via any of a wired and a wireless connection.

The display 130 can also render an estimated quantity of the blood and/or red blood cell content of one or more physical samples, a current total estimated red blood cell loss or blood loss of the patient, a current estimated intravascular blood volume or percentage blood volume of the patient, a hemorrhage rating or risk of the patient, or any other suitable blood-related variable or parameter of the patient. As described in U.S. patent application Ser. No. 13/738,919, this data can be presented in the form of a dynamic augmented reality overlay on top of a live video stream of an operating room and/or an imaging area for physical samples. For example, images from the optical sensor 110 can be relayed substantially in real time, through the processor 120, to the display 130 wherein the images are rendered concurrently with a current estimated hematocrit of the patient, an estimated blood volume of a recent physical sample, and a total estimated patient blood loss. The display 130 can also render any of the foregoing or other data in table, chart, or graphical form, such as multiple time-dependent hematocrit estimates. The display 130 can also render any of an image of a previous physical sample, a patient risk level (e.g., risk of hypovolemic shock), a hemorrhage classification of the patient, and/or a warning or suggestion, such as to begin a blood transfusion. Any of these data, warnings, and/or suggestions can also be depicted across multiple screens or menus or made accessible through the display 130 and/or interface 102 in any other suitable way.

As shown in FIG. 9, one variation of the system 100 further includes an alarm module 170, wherein the software module further triggers the alarm module in response to the estimated hematocrit of the patient falling outside a predefined range of suitable hematocrit values. Generally, the alarm module 170 functions to audibly and/or visually alert a user, such as a surgeon, anesthesiologist, or nurse, when a risk level of the patient falls outside of a suitable range. For example, the alarm module 170 can include a speaker, buzzer, or other type of sound driver. In another example, the alarm module 170 includes a digital alarm module that is rendered on the display, such as a flashing red box around a patient hematocrit value rendered on the display 130 or a large text-based warning that is displayed over the other data rendered on the display 130.

In one example implementation, the software module 122 triggers the alarm module 170 in response to an estimated patent hematocrit that falls outside a predefined range of safe hematocrit values, which can be based on the age, gender, health status, demographic, etc. of the patient. For example, the predefined range of safe hematocrit values for a male patient between the ages of 20 and 60 can be 0.39 to 0.50, whereas the predefined range of safe hematocrit values for a female patient between the ages of 20 and 60 can be 0.36 to 0.44. In another example implementation, the software module 122 triggers the alarm module 170 in response to an estimated total patient red blood cell loss that falls outside a predefined maximum percentage of loss of the estimated total initial red blood cell count of the patient. For example, the software module 122 can trigger the alarm module when the patient has lost more than 20% of his initial red blood cell count. In yet another example implementation, the software module 122 triggers the alarm module 170 in response to an estimated increase in intravascular fluid volume of patient that exceeds a threshold increase over the initial patient blood volume, such as a 10% increase over the initial patient blood volume. However, the software module 122 can trigger the alarm module 170 in response to any other blood-related value.

As shown in FIG. 10, one variation of the system 100 further includes a handheld housing 140 configured to contain the optical sensor 110, the processor 120, and the display 130. The handheld housing 140, with optical sensor 110, processor 120, and display 130, can define a handheld (mobile) electronic device capable of estimating patient hematocrit in any number of suitable environments, such as in an operating room or a delivery room. The handheld housing 140 can be of a medical-grade material such that the system 100 that is a handheld electronic device can be suitable for use in an operating room or other medical or clinical setting. For example, the housing can be medical-grade stainless steel, such as 316L stainless steel, a medical-grade polymer, such as high-density polyethylene (HDPE), or a medical-grade silicone rubber. However, the housing can be of any other material or combination of materials.

As shown in FIG. 10, one variation of the system 100 includes a wireless communication module 150 that communicates the estimated quantity red blood cell content of the physical sample, the estimated blood volume of the physical sample, and/or the estimate patient hematocrit to a remote server that stores and maintains an electronic medical record of the patient. The system 100 can also update the medical record with estimated blood loss over time, patient risk level, hemorrhage classification, and/or other blood-related metrics. The patient medical record can therefore be updated substantially automatically during a medical event, such as during a surgery or childbirth.

The systems and methods of the embodiments can be embodied and/or implemented at least in part as a machine configured to receive a computer-readable medium storing computer-readable instructions. The instructions are executed by computer-executable components integrated with the system 100, the optical sensor, the processor, the display, hardware/firmware/software elements of a system or handheld computing device, or any suitable combination thereof. Other systems and methods of the embodiments can be embodied and/or implemented at least in part as a machine configured to receive a computer-readable medium storing computer-readable instructions. The instructions are executed by computer-executable components integrated by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component is a processor but any suitable dedicated hardware device can (alternatively or additionally) execute the instructions.

As a person skilled in the art will recognize from the previous detailed description and from the figures and claims, modifications and changes can be made to the preferred embodiments of the invention without departing from the scope of this invention defined in the following claims.

We claim:

1. A method for managing blood loss of a patient, performed by one or more processors executing instructions in memory, the method comprising:
   receiving an image of a physical sample;
   extracting a color-related value from an area of the image corresponding to the physical sample;
   estimating a blood volume indicator of the physical sample according to the extracted color-related value;
   estimating a patient blood loss based on the blood volume indicator;
   estimating a euvolemic patient hematocrit based on an estimated patient blood volume and the estimated patient blood loss;
   receiving a measured patient hematocrit;
   generating a volemic status indicator based on a comparison between the measured patient hematocrit and the estimated euvolemic patient hematocrit; and
   displaying the volemic status indicator on a display.

2. The method of claim 1, further comprising tracking a quantity of a fluid administered to the patient intravenously and estimating an intracirculatory patient hematocrit based on a previous patient hematocrit, the estimated patient blood loss, a quantity of a fluid administered to the patient, and the estimated patient blood volume.

3. The method of claim 2, further comprising extrapolating a volume of insensible patient fluid loss from a difference between the estimated intracirculatory patient hematocrit and the measured patient hematocrit.

4. The method of claim 2, further comprising estimating an effectiveness of the fluid administered to the patient to replenish blood volume losses based on a difference between the estimated intracirculatory patient hematocrit and the estimated euvolemic patient hematocrit.

5. The method of claim 2, further comprising plotting the estimated intracirculatory patient hematocrit and a set of previous estimated intracirculatory patient hematocrits in a first time-dependent chart and plotting a volume of fluid administered to the patient in a second time-dependent chart.

6. The method of claim 2, wherein tracking the quantity of the fluid administered to the patient intravenously comprises tracking intravenous administration of allogeneic blood from a blood transfusion bag to the patient, wherein estimating the intracirculatory patient hematocrit comprises estimating the intracirculatory patient hematocrit further based on a hematocrit of allogeneic blood in the transfusion bag.

7. The method of claim 6, wherein tracking the quantity of the fluid administered to the patient intravenously comprises receiving a second image of the blood transfusion bag, extracting a color-related feature from an area of the second image corresponding to the blood transfusion bag, and estimating the hematocrit of allogeneic blood in the blood transfusion bag based on the color-related feature.

8. The method of claim 1, wherein estimating the patient blood loss further comprises displaying a total estimated blood loss within a time-dependent chart according to the estimated patient blood loss and previous estimated blood volumes of a set of previous physical samples.

9. The method of claim 1, further comprising triggering an alarm in response to a volemic status indicator that exceeds a threshold volemic status indicator.

10. The method of claim 1, wherein estimating the euvolemic patient hematocrit comprises estimating the euvolemic patient hematocrit according to a euvolemic blood model specifying intracirculatory replenishment of a total estimated volume of patient blood loss with saline.

11. The method of claim 1, wherein generating the volemic status indicator comprises generating a time-dependent chart comprising the volemic status indicator and a set of previous volemic status indicators.

12. The method of claim 11, further comprising predicting a future volemic status indicator according to a difference between the volemic status indicator and a previous volemic status indicator and triggering an alarm in response to the previous volemic status indicator that exceeds a threshold volemic status indicator.

13. method of claim 1, wherein estimating the euvolemic patient hematocrit comprises estimating an initial patient blood volume according to a weight of the patient, a height of the patient, a gender of the patient, and an age of the patient.

14. The method of claim 1, wherein generating the volemic status indicator comprises receiving measured patient hematocrits from an optical intracirculatory hematocrit monitor on a regular time interval, and wherein estimating the euvolemic patient hematocrit comprises estimating the euvolemic patient hematocrit further based on a previous measured patient hematocrit output by the optical intracirculatory hematocrit monitor.

15. The method of claim 1, wherein receiving the image of the physical sample comprises receiving a static color image, from an optical sensor, of the physical sample that comprises one of a surgical gauze sponge, a surgical towel, a surgical dressing, a surgical suction canister, and a cell salvage canister.

16. The method of claim 1, wherein extracting the color-related value from the area of the image comprises extracting a color intensity value of a set of pixels within the area of the image, wherein estimating the blood volume indicator of the physical sample comprises implementing a parametric model to transform the color intensity value into a quantity of red blood cells in the physical sample.

17. The method of claim 1, wherein estimating the patient blood loss comprises updating a total estimated blood loss volume of the patient with an estimated blood volume in the physical sample according to the extracted color-related value from the area of the image.

18. A method for managing blood loss of a patient, performed by one or more processors executing instructions in memory, the method comprising:
   receiving an image of a physical sample;
   extracting a color-related value from an area of the image corresponding to the physical sample;
   estimating a blood volume indicator of the physical sample according to the extracted color-related value;

estimating a patient blood loss based on the blood volume indicator;

estimating a euvolemic patient hematocrit based on an estimated patient blood volume and the estimated patient blood loss;

receiving a measured patient hematocrit;

generating a volemic status indicator based on a comparison between the measured patient hematocrit and the estimated euvolemic patient hematocrit; and triggering an alarm if the volemic status indicator exceeds a threshold value.

19. The method of claim 18, wherein the alarm is an audible or visual alarm.

* * * * *